US007001926B2

(12) United States Patent
Pinney et al.

(10) Patent No.: US 7,001,926 B2
(45) Date of Patent: Feb. 21, 2006

(54) TUBULIN BINDING AGENTS AND CORRESPONDING PRODRUG CONSTRUCTS

(75) Inventors: Kevin G. Pinney, Woodway, TX (US); Vani P. Mocharla, San Diego, CA (US); Zhi Chen, Hamden, CT (US); Anjan Ghatak, deceased, late of Salt Lake City, UT (US); by Usha R. Ghatak, legal representative, West Bengal (IN); Mallinath Hadimani, Waco, TX (US); Jimmy Kessler, Sugarland, TX (US); James M. Dorsey, Durham, NC (US); Klaus Edvardsen, Klampenborg (DK); David J. Chaplin, Oxford (GB); Joseph Prezioso, Boston, MA (US)

(73) Assignees: Oxigene, Inc., Waltham, MA (US); Baylor University, Waco, TX (US)

( * ) Notice: Subject to any disclaimer, the term of this patent is extended or adjusted under 35 U.S.C. 154(b) by 62 days.

(21) Appl. No.: 10/404,525

(22) Filed: Apr. 1, 2003

(65) Prior Publication Data

US 2004/0043969 A1   Mar. 4, 2004

Related U.S. Application Data

(63) Continuation-in-part of application No. 09/804,280, filed on Mar. 12, 2001, now Pat. No. 6,593,374.

(60) Provisional application No. 60/188,295, filed on Mar. 10, 2000.

(51) Int. Cl.
*A61K 31/075* (2006.01)
*C07C 41/00* (2006.01)

(52) U.S. Cl. ..................... 514/721; 568/633

(58) Field of Classification Search ............... 568/633; 514/721
See application file for complete search history.

(56) References Cited

U.S. PATENT DOCUMENTS

| | | | |
|---|---|---|---|
| 3,210,434 A * | 10/1965 | Chapman | 585/320 |
| 3,515,746 A * | 6/1970 | Bencze | 560/56 |
| 3,538,227 A * | 11/1970 | Bencze | 514/571 |
| 3,754,934 A * | 8/1973 | Pittet et al. | 426/537 |
| 3,879,432 A * | 4/1975 | Buchholz et al. | 554/5 |
| 4,133,814 A | 1/1979 | Jones et al. | |
| 4,656,187 A | 4/1987 | Black et al. | |
| 5,532,382 A | 7/1996 | Carlson et al. | |
| 5,596,106 A | 1/1997 | Cullinan et al. | |
| 5,886,025 A | 3/1999 | Pinney | |
| 5,952,350 A | 9/1999 | Cullinan et al. | |
| 5,958,916 A | 9/1999 | Bryant et al. | |
| 6,162,930 A | 12/2000 | Pinney et al. | |
| 6,350,777 B1 | 2/2002 | Pinney et al. | |
| 6,593,374 B1 * | 7/2003 | Pinney et al. | 514/721 |
| 6,773,702 B1 * | 8/2004 | Pero et al. | 424/93.21 |

FOREIGN PATENT DOCUMENTS

| | | |
|---|---|---|
| EP | 1028110 | 8/2000 |
| WO | WO 96/40137 | 12/1996 |
| WO | WO 98/39323 | 9/1998 |
| WO | WO 01/68654 | 9/2001 |
| WO | WO 02/060872 | 9/2001 |
| WO | WO 01/77093 | 10/2001 |
| WO | WO 01/79180 | 10/2001 |

OTHER PUBLICATIONS

CA 63: 62817, Rutschmann et al, 1965.*
CA 129: 189097, 1998.*
CA 46: 17739 , Ciba Ltd. 1952.*
CA 70:57529 , Bencze, William L. , 1969.*
CA 108: 131316 , Kralovec et al. 1988.*
Boyd et al., "Some Practical Consideration and Applications of the National Cancer Institute In Vitro Anticancer Drug Discovery Screen", *Drug Development Research*. 34:91-109 (1995).
Churcher et al., "Synthesis of the Antitumor Agent Aglycon (±)-Calicheamicinone Using an o-Quinone Monoketal Strategy", *J. Am. Chem. Soc.*, 120: 13350-10358 (1998).
Clive et al., "Synthesis of (±)-Calicheamicinone by Two Methods", *J. Am. Chem Soc.*, 120: 10332-10349 (1998).
Cushman et al., "Synthesis of Analogs of 2-Methoxyestradiol with Enhanced Inhibitory Effects on Tubulin Polymerization and Cancer Cell Growth", *J. Med. Chem.*, 40: 2323-2334 (1997).
Cushman et al., "Synthesis, Antibulin and Antimitotic Activity, and Cytotoxicity of Analogs of 2-Methoyestradiol, an Endogenous Mammalian Metabolite of Estradiol that Inhibits Tubulin Polymerization by Binding to the Colchicine Binding Site", *J. Med. Chem.*, 38: 2041-2049 (1995).

(Continued)

*Primary Examiner*—Deborah C. Lambkin
(74) *Attorney, Agent, or Firm*—Mintz,Levin,Cohn,Ferris,Glovsky and Popeo, P.C.; Ivor R. Elrifi; Naomi S. Biswas

(57) ABSTRACT

A diverse set of tubulin binding agents have been discovered which are structurally characterized, in a general sense, by a semi-rigid molecular framework capable of maintaining aryl-aryl, pseudo pi stacking distances appropriate for molecular recognition of tubulin. In phenolic or amino form, these ligands may be further functionalized to prepare phosphate esters, phosphate salts, phosphoramidates, and other prodrugs capable of demonstrating selective targeting and destruction of tumor cell vasculature.

28 Claims, 14 Drawing Sheets

OTHER PUBLICATIONS

D'Amato et al., "2-Methoxyestradiol, an Endogenous Mammalian Metabolite, Inhibits Tubulin Polymerization by Interacting at the Colchicines Site", *Proc. Natl. Acad. Sci.*, 91: 3964-3968 (1994).

Flynn et al., A Novel Palladium-Mediated Coupling Approach to 2,3-Disubstituted.

Benzo[b]thiophenes and Its Application to the Synthesis of Tublin Binding Agents, *Organic Letters*, 3: 651-654 (2001).

Grese et al., "Structure-Activity Relationships of Selective Estrogen Receptor Modulators: Mofdifications to the 2-Arylbenzothiophene Core of Raloxifene", *J. Med. Chem*, 40: 146-167 (1997).

Hamel et al., "Interaction of 2-Methoxyestradiol, an Endogenous Mammalian Metabolite, with Unpolymerized Tubulin and with Tubulin Polymers", *Biochemistry*, 35: 1304-1310 (1995).

Jones et al., "Structure-Activity Studies in a Series of 3-Aroyl-2-arylbenzo[b]thiophene Derivatives Leading to [6-Hydroxy-2-(4-hydroxyphenyl)benzo [b]thien-3-yl][4-[2-(1-piperidinyl)ethoxy]-phenyl]methanone Hydrochloride (LY156758), a Remarkably Effective Estrogen Antagonist with only Minimal Intrinsic Estrogenicity" :*J. Med. Chem.*, 27: 1057-1066 (1984).

Myers et al., "A Convergent Synthetic Route to (+)-Dynemicin A and Analogs of Wide Structural Variability" *J. Am. Chem. Soc.*, 119: 6072-6094 (1997).

Mullica et al., "characterization and Structural Analyses of Trimethoxy and Triethoxybenzo[b]thiophene", *J. Chem. Cryst.*, 28: 289-295 (1998).

Palkowitz et al., "Discovery and Synthesis of [6]Hydroxy-3-[4-[2-(1-piperidinyl)ethoxy]phenoxy]-2-(4-hydroxyphenyl)benzo[b]thiophene: A Novel, Highly Potent, Selective Estrogen Receptor Modulator", *J. Med. Chem.*, 40: 1407-1416 (1997).

Pinney et al., "A New Anti-Tubulin Agent Containing the Benzo[b]thiophene Ring System, Bioorganic and Medicinal Chemistry Letter", 9: 1081-1086 (1999).

* cited by examiner

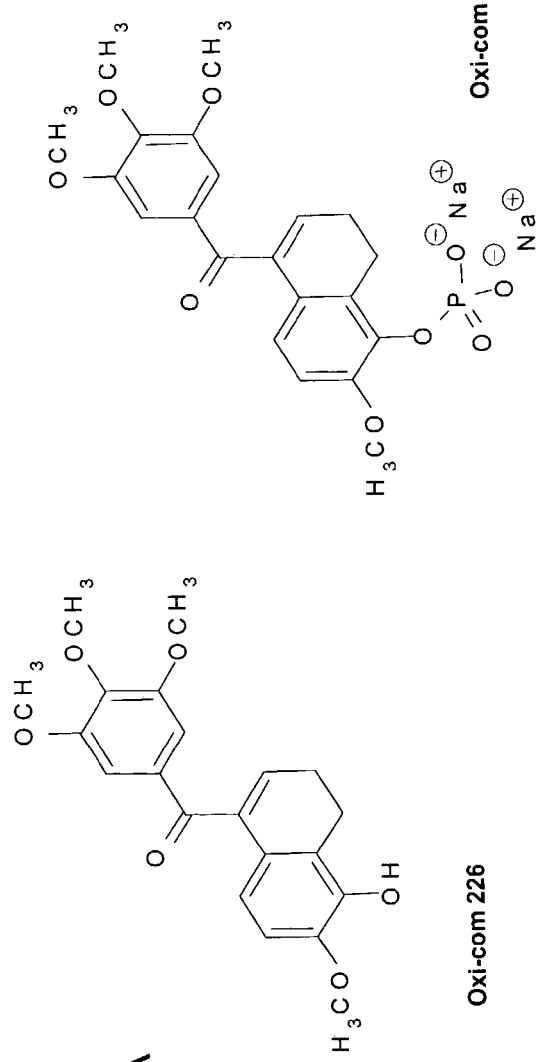
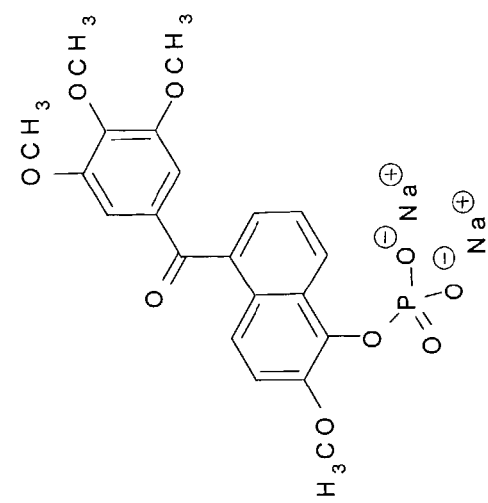
Figure 7A
Figure 7B

TUBULIN BINDING AGENTS AND CORRESPONDING PRODRUG CONSTRUCTS

CROSS-REFERENCE TO RELATED APPLICATIONS

This is a Continuation-In-Part of U.S. patent application Ser. No. 09/804,280, filed Mar. 12, 2001 now U.S. Pat. No. 6,593,374, which itself claims priority to U.S. provisional patent application Ser. No. 60/188,295 filed on Mar. 10, 2000. This application also claims the priority benefit of copending U.S. patent application Ser. No. 10/218,833, filed Aug. 14, 2002, which itself claims priority to both U.S. patent application Ser. No. 09/505,402, filed Feb. 16, 2000 and U.S. provisional patent application Ser. No. 60/120,478, filed Feb. 18, 1999. Attention is called to U.S. Pat. No. 6,162,930 issued to Pinney et al. on Dec. 19, 2000, which is incorporated in its entirety by reference herein. The following citations are incorporated in pertinent part by reference herein for the reasons cited.

BACKGROUND OF THE INVENTION

The cytoskeletal protein tubulin is among the most attractive therapeutic drug targets for the treatment of solid tumors. A particularly successful class of chemotherapeutics mediates its anti-tumor effect through a direct binding interaction with tubulin. This clinically-promising class of therapeutics, called Tubulin Binding Agents, exhibit potent tumor cell cytotoxicity by efficiently inhibiting the polymerization of $\alpha\beta$-tubulin heterodimers into the microtubule structures that are required for facilitatation of mitosis or cell division (Hamel, Medicinal Research Reviews, 1996).

Currently, the most recognized and clinically useful antitumor agents are Vinca Alkaloids, such as Vinblastine and Vincristine (Owellen et al, Cancer Res., 1976; Lavielle et al, J. Med. Chem., 1991) along with Taxanes such Taxol (Kingston, J. Nat. Prod., 1990; Schiff et al, Nature, 1979; Swindell et al, J. Cell Biol., 1981). Additionally, natural products such as Rhizoxin (Nakada et al, Tetrahedron Lett., 1993; Boger et al, J. Org. Chem., 1992; Rao, et al, Tetrahedron Lett., 1992; Kobayashi et al, Pure Appl. Chem., 1992; Kobayashi et al, Indian J. Chem., 1993; Rao et al, Tetrahedron Lett., 1993), the Combretastatins (Lin et al, Biochemistry, 1989; Pettit et al, J. Nat. Prod., 1987; Pettit et al, J. Org. Chem., 1985; Pettit et al, Can. J. Chem., 1982; Dorr et al, Invest. New Drugs, 1996), Curacin A (Gerwick et al, J. Org. Chem., 59:1243, 1994), Podophyllotoxin (Hammonds et al, J. Med. Microbiol, 1996; Coretese et al, J. Biol. Chem., 1977), Epothilones A and B (Nicolau et al., Nature, 1997), Dolastatin-10 (Pettit et al, J. Am. Chem. Soc., 1987; Pettit et al, Anti-Cancer Drug Des., 1998), and Welwistatin (Zhang et al, Molecular Pharmacology, 1996), as well as certain synthetic analogues including Phenstatin (Pettit G R et al., J. Med. Chem., 1998), 2-styrylquinazolin-4(3H)-ones ("SQOs", Jiang et al, J. Med. Chem., 1990), and highly oxygenated derivatives of cis- and trans-stilbene and dihydrostilbene (Cushman et al, J. Med. Chem., 1991) are all known to mediate their tumor cytotoxic activity through tubulin binding and subsequent inhibition of mitosis.

Normally, during the metaphase of cell mitosis, the nuclear membrane has broken down and tubulin is able to form centrosomes (also called microtubule organizing centers) which facilitate the formation of a microtubule spindle apparatus to which the dividing chromosomes become attached. Subsequent polymerization and depolymerization of the spindle apparatus mitigates the separation of the daughter chromosomes during anaphase such that each daughter cell contains a full complement of chromosomes. As antiproliferatives or antimitotic agents, Tubulin Binding Agents exploit the relatively rapid mitosis that occurs in proliferating tumor cells. By binding to tubulin and inhibiting the formation of the spindle apparatus in a tumor cell, the Tubulin Binding Agent can cause significant tumor cell cytotoxicity with relatively minor effects on the slowly-dividing normal cells of the patient.

The exact nature of tubulin binding site interactions remain largely unknown, and they definitely vary between each class of Tubulin Binding Agent. Photoaffinity labeling and other binding site elucidation techniques have identified three key binding sites on tubulin: 1) the Colchicine site (Floyd et al, Biochemistry, 1989; Staretz et al, J. Org. Chem., 1993; Williams et al, J. Biol. Chem., 1985; Wolff et al, Proc. Natl. Acad. Sci. U.S.A., 1991),2) the Vinca Alkaloid site (Safa et al, Biochemistry, 1987), and 3) a site on the polymerized microtubule to which taxol binds (Rao et al, J. Natl. Cancer Inst., 1992; Lin et al, Biochemistry, 1989; Sawada et al, Bioconjugate Chem, 1993; Sawada et al, Biochem. Biophys. Res. Commun., 1991; Sawada et al, Biochem. Pharmacol., 1993). An important aspect of this work requires a detailed understanding, at the molecular level, of the "small molecule" binding domain of both the $\alpha$ and $\beta$ subunits of tubulin. The tertiary structure of the $\alpha,\beta$ tubulin heterodimer was reported in 1998 by Downing and co-workers at a resolution of 3.7 Å using a technique known as electron crystallography (Nogales et al, Nature, 1998). This brilliant accomplishment culminates decades of work directed toward the elucidation of this structure and should facilitate the identification of small molecule binding sites, such as the colchicine site, using techniques such as photoaffinity and chemical affinity labeling (Chavan et al, Bioconjugate Chem., 1993; Hahn et al, Photochem. Photobiol., 1992).

An aggressive chemotherapeutic strategy for the treatment and maintenance of solid tumor cancers continues to rely on the development of architecturally new and biologically more potent Tubulin Binding Agents which mediate their effect through a direct binding interation with tubulin. The present invention addresses this urgent need by providing a structurally novel class of Tubulin Binding Agent compositions with potent antiproliferative activity and tumor cell cytotoxicity. In addition, the present invention provides the important discovery that corresponding prodrug constructs of these agents have selective effects on the tumor vasculature which are independent of its primary antimitotic effects on the tumor itself. These agents are capable of selectively shutting down the flow of blood to a tumor causing secondary tumor cell death. Thus the present compositions have expanded clinical utility over known tubulin binding agents.

SUMMARY OF THE INVENTION

The present invention relates to a discovery of dihydronapthalene compounds that result from the judicious combination of a non-tubulin binding molecular template which, when suitably modified with structural features such as phenolic moieties and arylalkoxy groups, is found to function as a Tubulin Binding Agent capable of inhibiting tubulin polymerization and tumor cell proliferation.

One important aspect of the present invention provides a compound of the following general formula I:

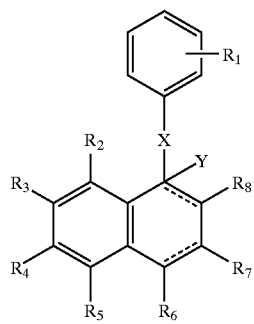

Formula I wherein:
$R_1$ is optionally H, Halogen, or Lower Alkoxy,
R2 through R8 are independently selected from the group consisting of H, OH, Amine, Lower Alkoxy, Phosphate, Phosphoramidate, or Amino Acid Acyl Group,
----- is optionally a single covalent bond or double covalent bond,
X is optionally a single covalent bond or a carbonyl group, and
Y is optionally H or OH.

In a more specific embodiment, the present invention focuses on dihydronaphthalene derivatives, particularly a compound of the following general Formula Ia:

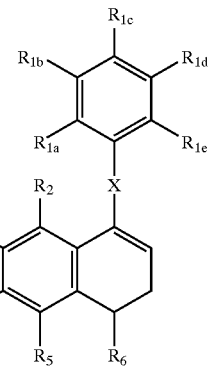

Formula Ia $R_{1a}$, $R_{1b}$, $R_{1c}$, $R_{1e}$, and $R_{1f}$ are independently selected from the group consisting of H, Halogen, or Lower Alkoxy,
R2 through R6 are independently selected from the group consisting of H, OH, Halogen, Amine, Lower Alkoxy, Phosphate, Phosphoramidate, or Amino Acid Acyl; and
X is a single covalent bond or a carbonyl group.

Compounds of Formula Ia can be synthesized according to the following general synthetic scheme:

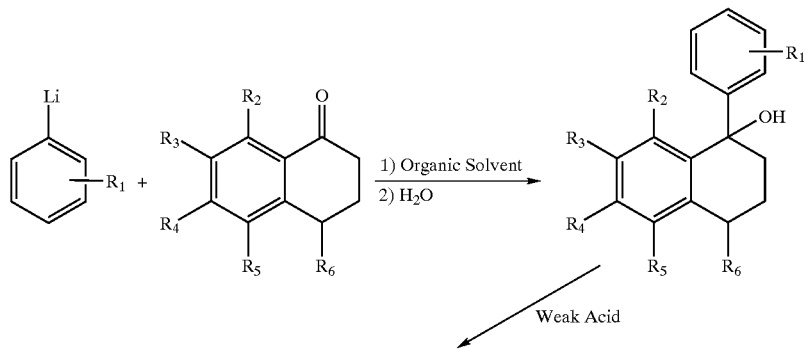

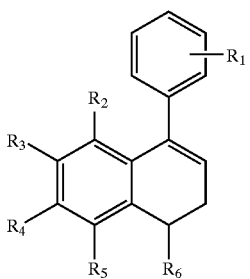

A particularly preferred dihydronaphthalene derivative is the compound of the following structure (1):

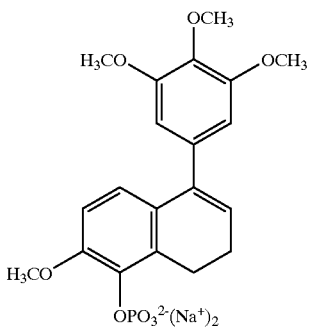

(1)

In a further specific embodiment, the compound of the following general Formula Ib:

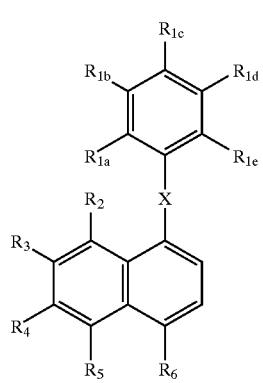

(Ib)

wherein:
$R_{1a}$, $R_{1b}$, $R_{1c}$, $R_{1e}$, and $R_{1f}$ are independently selected from the group consisting of H, Halogen, or Lower Alkoxy,
R2 through R6 are independently selected from the group consisting of H, OH, Halogen, Amine, Lower Alkoxy, Phosphate, Phosphoramidate, or Amino Acid Acyl; and
X is a single covalent bond or a carbonyl group.

In a second aspect, the invention contemplates methods of contacting a tubulin-containing system with an effective amount of a compound of Formula I or Formula Ib. Methods are also provided for treating a warm-blooded animal afflicted with a neoplastic disease comprising administering an effective amount of compound capable of inhibiting the proliferation of the neoplastic disease. In a preferred embodiment, the antiproliferative effect has the direct result of causing tumor cell cytotoxicity due to inhibition of mitosis.

In a third aspect, the invention broadly contemplates the provision of a method for treating a warm-blooded animal having a vascular proliferative disorder comprising administering an effective amount of a compound of the present invention to achieve targeted vascular toxicity at a locality of proliferating vasculature, wherein in the proliferating vasculature is malignant or nonmalignant.

In yet another aspect, the invention broadly contemplates the provision of a method for administering an effective amount of a compound of the present invention to selectively reduce the flow of blood to at least a portion of a neoplastic region, thereby causing substantial necrosis of tissue in the neoplastic region without substantial necrosis of tissue in adjoining regions. In a preferred embodiment, the effect of reduced tumor blood flow is reversible so that normal tumor blood flow is restored following cessation of treatment.

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

BRIEF DESCRIPTION OF THE DRAWINGS

FIG. 7A) depicts an exemplary aroyl-substituted dihydronaphthalene tubulin binding agents and corresponding prodrug constructs; and B) an exemplary aroyl-substituted naphthalene prodrug construct.

DETAILED DESCRIPTION OF THE INVENTION

Figure 1:
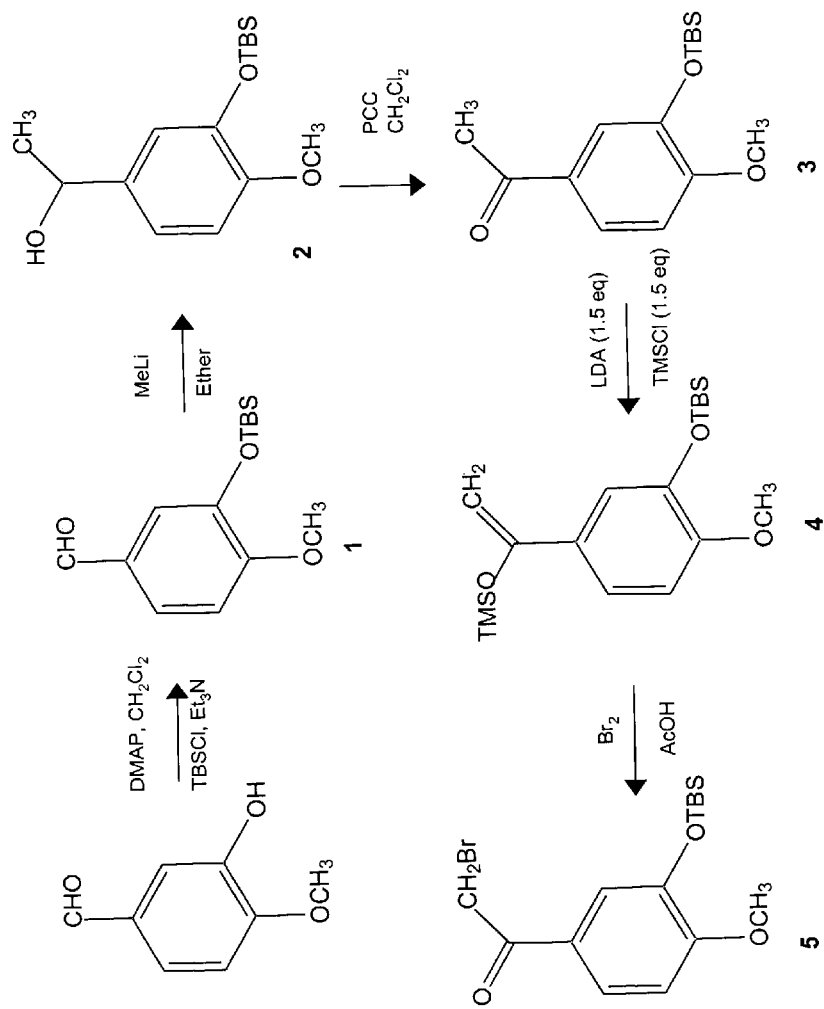
FIG. 1 illustrates a synthetic route for large-scale preparation of starting material required for synthesis of tubulin binding agents.

The compounds of the present invention, demonstrate remarkable cytotoxicity against a variety of human cancer cell lines. The ability of an agent to inhibit tubulin polymerization and microtubule formation is an important property of many anticancer agents. Disruption of microtubules that comprise the cytoskeleton and mitotic spindle apparatus can interfere dramatically with the ability of a cell to successfully complete cell division. The compounds of the present invention are highly cytotoxic to actively proliferating cells, inhibiting the mitosis and often causing selective apoptosis of tumor cells, while leaving normal quiescent cells relatively unaffected.

Further significance is given to new drugs that bind to the colchicine site since it has recently been shown that many tubulin binding agents which bind to this site also demonstrates activity on against malignant proliferating vasculature. Antivascular chemotherapy is an emerging area of cancer chemotherapy which centers on the development of drugs, called Vascular Targeting Agents ("VTAs") or vascular damaging agent, that selectively target the vasculature of tumor cells rather than the tumor cells themselves. Much of the research in anti-vascular cancer therapy has focused on understanding the process of new blood vessel formation, known as angiogenesis, and identifying anti-angiogenic agents which inhibit the formation of new blood vessels. Angiogenesis is characterized by the proliferation of tumor endothelial cells and generation of new vasculature to support the growth of a tumor. This growth is stimulated by certain growth factors produced by the tumor itself. One of these growth factors, Vascular Endothelial Growth Factor ("VEGF"), is relatively specific towards endothelial cells, by virtue of the restricted and up-regulated expression of its cognate receptor. Various anti-angiogenic strategies have been developed to inhibit this signaling process at one or more steps in the biochemical pathway in order to prevent the growth and establishment of the tumor vasculature. However, anti-angiogenic therapies act slowly and must be chronically administered over a period of months to years in order to produce a desired effect.

In contrast to Anti-angiogeneic agents, VTAs attack solid tumors by selectively targeting the established tumor vasculature and cause extensive shutdown of tumor blood flow. A single dose of VTA can cause a rapid and selective shutdown of the tumor neovasculature within a period of minutes to hours, leading eventually to tumor necrosis by induction of hypoxia and nutrient depletion. This vascular-mediated cytotoxic mechanism of VTA action is quite divorced from that of anti-angiogenic agents which inhibit the formation of new tumor vascularization, rather than interfering with the existing tumor vasculature. Other agents have been known to disrupt tumor vasculature but differ in that they also manifest substantial normal tissue toxicity at their maximum tolerated dose. In contrast, genuine VTAs retain their vascular shutdown activity at a fraction of their maximum tolerated dose. Combretastatin A-4 Disodium Phosphate Prodrug ("CA4DP") is the lead drug of a group of VTAs currently in clinical trials (U.S. Pat. No. 5,561,122; Chaplin et al, Anticancer Res., 1999; Tozer et al, Cancer Res., 1999; Pettit and Rhodes, Anti-Cancer Drug Des., 1998; Iyer et al, Cancer Res., 1998; Dark et al, Cancer Res., 1997;). Other Tubulin binding VTAs that have been discovered include the Colchicinoid ZD6126 (Davis et al., Cancer Research, 2002) and the Combretastatin analog AVE8032 (Lejeune et al, Proceedings of the AACR., 2002). It is thought that Tubulin-binding VTAs selectively destabilize the microtubule cytoskeleton of tumor endothelial cells, causing a profound alteration in the shape of the cell which ultimately leads to occlusion of the tumor blood vessel and shutdown of blood flow to the tumor (Kanthou, Blood, 2002). Thus the invention provides the discovery that the compounds of Formulas I and Ia as well as analogs thereof, are vascular targeting agents (VTAs), and thus are useful for the treatment of malignant vascular proliferative disorders, such as solid tumor cancers, as well as other nonmalignant vascular proliferative disorders, such as retinal neovascularization and restenosis.

In one embodiment, the present invention is directed to the administration of a vascular targeting agent ("VTA"), particularly a tubulin binding agent, for the treatment of malignant or non-malignant vascular proliferative disorders in ocular tissue.

Neovascularization of ocular tissue is a pathogenic condition characterized by vascular proliferation and occurs in a variety of ocular diseases with varying degrees of vision failure. The administration of a VTA for the pharmacological control of the neovascularization associated with non-malignant vascular proliferative disorders such as wet macular degeneration, proliferative diabetic retinopathy or retinopathy of prematurity would potentially benefit patients for which few therapeutic options are available. In another embodiment, the invention provides the administration of a VTA for the pharmacological control of neovascularization associated with malignant vascular proliferative disorders such as ocular tumors.

The blood-retinal barrier (BRB) is composed of specialized nonfenestrated tightly-joined endothelial cells that form a transport barrier for certain substances between the retinal capillaries and the retinal tissue. The nascent vessels of the cornea and retina associated with the retinopathies are aberrant, much like the vessels associated with solid tumors. Tubulin binding agents, inhibitors of tubulin polymerization and vascular targeting agents, may be able to attack the aberrant vessels because these vessels do not share architectural similarities with the blood retinal barrier. Tubulin binding agents may halt the progression of the disease much like they do with a tumor-vasculature.

The compounds of the present invention may are also contemplated for use in the treatment of vascular disease, particularly atheroscleorsis and restenosis. Atherosclerosis is the most common form of vascular disease and leads to insufficient blood supply to critical body organs, resulting in heart attack, stroke, and kidney failure. Additionally, atherosclerosis causes major complications in those suffering from hypertension and diabetes, as well as tobacco smokers. Atherosclerosis is a form of chronic vascular injury in which some of the normal vascular smooth muscle cells ("VSMC") in the artery wall, which ordinarily control vascular tone regulating blood flow, change their nature and develop "cancer-like" behavior. These VSMC become abnormally proliferative, secreting substances (growth factors, tissue-degradation enzymes and other proteins) which enable them to invade and spread into the inner vessel lining, blocking blood flow and making that vessel abnormally susceptible to being completely blocked by local blood clotting, resulting in the death of the tissue served by that artery.

Restenosis, the recurrence of stenosis or artery stricture after corrective surgery, is an accelerated form of atherosclerosis. Recent evidence has supported a unifying hypothesis of vascular injury in which coronary artery restenosis along with coronary vein graft and cardiac allograft atherosclerosis can be considered to represent a much accelerated form of the same pathogenic process that results in spontaneous atherosclerosis. Restenosis is due to a complex series of fibroproliferative responses to vascular injury involving potent growth-regulatory molecules, including platelet-derived growth factor (PDGF) and basic fibroblast growth factor (bFGF), also common to the later stages in atherosclerotic lesions, resulting in vascular smooth muscle cell proliferation, migration and neointimal accumulation.

Restenosis occurs after coronary artery bypass surgery (CAB), endarterectomy, and heart transplantation, and particularly after heart balloon angioplasty, atherectomy, laser ablation or endovascular stenting (in each of which one-third of patients redevelop artery-blockage (restenosis) by 6 months), and is responsible for recurrence of symptoms (or death), often requiring repeat revascularization surgery. Despite over a decade of research and significant improvements in the primary success rate of the various medical and surgical treatments of atherosclerotic disease, including angioplasty, bypass grafting and endarterectomy, secondary failure due to late restenosis continues to occur in 30–50% of patients.

The most effective way to prevent this disease is at the cellular level, as opposed to repeated revascularization surgery which can carry a significant risk of complications or death, consumes time and money, and is inconvenient to the patient.

As used herein, the following terms in quotations shall have the indicated meanings, whether in plural or singular form:

"Amino acid acyl group" in the amino acid acylamino group is an acyl group derived from the amino acid. The amino acids may be enumerated by α-amino acids, β-amino acids and γ-amino acids. Examples of preferred amino acids include glycine, alanine, leucine, serine, lysine, glutamic acid, asparatic acid, threonine, valine, isoleucine, ornithine, glutamine, asparagines, tyrosine, phenylalanine, cysteine, methionine, arginine, β-alanine, tryptophan, proline, histidine, etc. The preferred amino acid is serine and the preferred amino acid acyl group is a serinamide.

"Amine" refers to a free amine $NH_2$ or a lower alkylamino.

"Animal" refers to any warm-blooded mammal, preferably a human.

"Alkyl" refers to a group containing from 1 to 8 carbon atoms and maybe straight chained or branched. An alkyl group is an optionally substituted straight, branched or cyclic saturated hydrocarbon group. When substituted, alkyl groups may be substituted with up to four substituent groups, R as defined, at any available point of attachment. When the alkyl group is said to be substituted with an alkyl group, this is used interchangeably with "branched alkyl group". Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents may include but are not limited to one or more of the following groups: halo (such as F, Cl, Br, I), haloalkyl (such as $CCl_3$ or $CF_3$), alkoxy, alkylthio, hydroxy, carboxy (—COOH), alkyloxycarbonyl (—C(O)R), alkylcarbonyloxy (—OCOR), amino (—$NH_2$), carbamoyl (—NHCOOR— or —OCONHR—), urea (—NHCONHR—) or thiol (—SH). Alkyl groups as defined may also comprise one or more carbon to carbon double bonds or one or more carbon to carbon triple bonds.

"Aryl" refers to groups with aromaticity, including 5- and 6-membered single-ring aromatic groups that may include from zero to four heteroatoms, as well as multicyclic systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. The aromatic ring can be substituted at one or more ring positions with such substituents as described above, as for example, halogen, hydroxyl, alkoxy, etc. The preferred aryl group of the present invention is a benzene ring.

"Aroyl" refers to the —(C=O)-aryl groups, wherein aryl is defined as hereinabove. The aryl group is bonded to the core compound through a carbonyl bridge.

"Cycloalkyl" is a species of alkyl containing from 3 to 15 carbon atoms, without alternating or resonating double bonds between carbon atoms. It may contain from 1 to 4 rings. Exemplary unsubstituted such groups include cyclopropyl, cyclobutyl, cyclopentyl, cyclohexyl, adamantyl, etc. Exemplary substituents include one or more of the following groups: halogen, alkyl, alkoxy, alkyl hydroxy, amino, nitro, cyano, thiol and/or alkylthio.

"Halogen" or "Halo" refers to chlorine, bromine, fluorine or iodine.

"Lower alkoxy" refers to —O-alkyl groups, wherein alkyl is as defined hereinabove. The alkoxy group is bonded to the core compound through the oxygen bridge. The alkoxy group may be straight chained or branched; although the straight-chain is preferred. Examples include methoxy, ethyloxy, propoxy, butyloxy, t-butyloxy, i-propoxy, and the like. Preferred alkoxy groups contain 1–4 carbon atoms, especially preferred alkoxy groups contain 1–3 carbon atoms. The most preferred alkoxy group is methoxy.

"Lower alkylamino" refers to a group wherein one or two alkyl groups is bonded to an amino nitrogen, i.e., NH(alkyl).

The nitrogen is the bridge connecting the alkyl group the core compound. Examples include NHMe, NHEt, NHPr, and the like.

"Prodrug" refers to a precursor form of the drug which is metabolically converted in vivo to produce the active drug. Preferred prodrugs of the present invention include the phosphate, phosphoramidate, or amino acid acyl groups as defined herein. The phosphate ester salt moiety may also include ($-$OP(O)(O-alkyl)$_2$ or ($-$OP(O)(O$-$NH$_4^+$)$_2$).

"Phenolic moiety" means herein a hydroxy group when it refers to an R group on an aryl ring.

"Phosphate", "Phosphate moiety", or "Phosphate prodrug salt" refers to phosphate ester salt moiety ($-$OP(O)(O$^-$M$^+$)$_2$), a phosphate triester moiety ($-$OP(O)(OR)$_2$) or a phosphate diester moiety ($-$OP(O)(OR)(O$^-$M$^+$), where M is a salt and R is chosen to be any appropriate alkyl or branched alkyl substituent (the two R groups may be the same alkyl group or may be mixed), or benzyl, or aryl groups. The salt M is advantageously Na, K and Li, but the invention is not limited in this respect.

"Phosphoramidate" refers to a phosphoamidate ester salt moiety ($-$NP(O)(O$^-$M$^+$)$_2$), a phosphoramidate diester moiety ($-$NP(O)(OR)$_2$), or a phosphamidate disalt moiety ($-$NP(O)(OR)(O$^-$M$^+$), where M is a salt and R is chosen to be any appropriate alkyl or branched alkyl substituent (the two R groups may be the same alkyl group or may be mixed), or benzyl, or aryl groups. The salt M is advantageously Na, K and Li, but the invention is not limited in this respect.

"Salt" is a pharmaceutically acceptable salt and can include acid addition salts such as the hydrochlorides, hydrobromides, phosphates, sulphates, hydrogen sulphates, alkylsulphonates, arylsulphonates, acetates, benzoates, citrates, maleates, fumarates, succinates, lactates, and tartrates; alkali metal cations such as Na, K, Li, alkali earth metal salts such as Mg or Ca or organic amine salts such as those disclosed in PCT International Application Nos. WO02/22626 or WO00/48606.

"Tubulin Binding Agent" shall refer to a ligand of tubulin or a compound capable of binding to either αβ-tubulin heterodimers or microtubules and interfering with the polymerization or depolymerization of microtubules.

"Tumors", "Cancers", or "Neoplastic Disease" shall be used interchangeably and include (but are not limited to) the following:

1) carcinomas, including that of the bladder, breast, colon, kidney, liver, lung, including small cell lung cancer, esophagus, gall bladder, ovary, pancreas, stomach, cervix, thyroid, prostate, and skin, including squamous cell carcinoma;
2) hematopoictic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkett's lymphoma;
3) hematopoietic tumors of myeloid lineage, including acute and chronic myelogenous leukemias, myelodysplastic syndrome and promyclocytic leukemia;
4) tumors of mesenchymal origin, including fibrosarcoma and rhabdomyosarcoma;
5) tumors of the central and peripheral nervous system, including astrocytoma, neuroblastoma, glioma and schwannomas; and
6) other tumors, including melanoma, seminoma, teratocarcinoma, osteosarcoma, xenoderoma pigmentosum, keratoctanthoma, thyroid follicular cancer, anaplastic thyroid cancer and Kaposi's sarcoma.

"Vascular toxicity" refers to the selective destruction, damage, or occlusion, whether reversible or irreversible, partial or complete, of proliferating vasculature.

"Malignant proliferating vasculature" refers to the endothelium, artery, blood vessel, or neovasculature formed by a malignant disease state, such as a tumor.

"Nonmalignant proliferating vasculature" refers to the endothelium, artery, blood vessel, or neovasculature formed by undesirable or pathological angiogenesis and that is associated with disease states other than a malignant disease state, including without limitation ocular diseases such wet or age-related macular degeneration, diabetic retinopathy, retinopathy of prematurity, diabetic molecular edema, uveitis, and corneal neovascularization, or other nonocular disease states such as psoriasis, rheumatoid arthritis, atheroma, restenosis, Kaposi's sarcoma, haemangioma, and in general, inflammatory diseases characterized by vascular proliferation.

"Antiproliferative" or "antimitotic" refer to the ability of the compounds of the present invention to directly inhibit the proliferation of tumor cells and impart direct cytotoxicity towards tumor cells.

"Treating" (or "treat") as used herein includes its generally accepted meaning which encompasses prohibiting, preventing, restraining, and slowing, stopping, or reversing progression, severity, of a resultant symptom. As such, the methods of this invention encompass both therapeutic and prophylactic administration.

"Effective amount" refers to the amount or dose of the compound, upon single or multiple dose administration to the patient, which provides the desired effect in the patient under diagnosis or treatment.

An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the species of mammal; its size, age, and general health; the specific disease involved,; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

A typical daily dose will contain from about 0.1 mg/kg to about 1000 mg/kg of the active compound of this invention. Preferably, daily doses will be about 10 mg/kg to about 100 mg/kg, and most preferably about 10 mg.

In effecting treatment of a patient afflicted with a condition, disease or disorder described herein, a compound of the present invention can be administered systemically in any form or mode which makes the compound bioavailable in effective amounts. Systemic administration may be accomplished by administration of a compound of the present invention into the bloodstream at a site which is separated by a measurable distance from the diseased or affected organ or tissue. For example, compounds of the present invention can be administered orally, parenterally, subcutaneously, intramuscularly, intravenously, transdermally, intranasally, rectally, buccally, and the like. Oral or intravenous administration is generally preferred for treating neoplastic disease or cancer. Alternatively, the compound may be administered non-systemically by local administration of the compound of the present invention directly at the diseased or affected organ or tissue. Treatment of ocular diseases characterized by the presence of non-malignant proliferative vasculature or neovascularization, can be achieved using non-systemic administration methods such as intravitreal injection, sub-Tenon's injection, ophthalmic drops, iontophoresis, topical formulation and implants and/or inserts. One skilled in the art of preparing formulations can readily select the proper form and mode of administration depending upon the particular characteristics of the compound selected, the disease state to be treated, the stage of the disease, and other relevant circumstances.

It will be understood by the skilled reader that all of the compounds used in the present invention are capable of forming salts, and that the salt forms of pharmaceuticals are commonly used, often because they are more readily crystallized and purified than are the free bases. In all cases, the use of the pharmaceuticals described above as salts is contemplated in the description herein, and often is preferred, and the pharmaceutically acceptable salts of all of the compounds are includes in the names of them.

According to another aspect, the present invention provides a pharmaceutical composition, which comprises a compound of the present invention or a pharmaceutically acceptable salt thereof as defined hereinabove and a pharmaceutically acceptable diluent or carrier.

The pharmaceutical compositions are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, micro-crystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well know in the art.

The compositions are preferably formulated in a unite dosage form, each dosage containing from about 1 mg to about 500 mg, more preferably about 5 mg to about 300 mg (for example 25 mg) of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

The compositions of the present invention may be formulated in a conventional manner using one or more pharmaceutically acceptable carriers. Thus, the active compounds of the invention may be formulated for oral, buccal, transdermal (e.g., patch), intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose of calcium phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form, of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in a powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension form a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

Tablets or capsules of the compounds may be administered singly or two or more at a time as appropriate. It is also possible to administer the compounds in sustained release formulations.

The physician will determine the actual dosage which will be most suitable for an individual patient and it will vary with the age, weight and response of the particular patient. The above dosages are exemplary of the average case. There can of course, be individual instances where higher or lower dosage ranges are merited, and such are within the scope of this invention.

The compounds of the present invention can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilizers an preservatives as may be required.

"Administering" means any of the standard methods of administering a compound to a subject, known to those skilled in the art. Examples include, but are not limited to intravenous, intramuscular or intraperitoneal administration.

The clonogenic toxicity may be increased by imbalancing $Ca^{2+}$ cytosolic levels or nucleotide pools or in combination thereof.

For the purposes of this invention "pharmaceutically acceptable carriers" means any of the standard pharmaceutical carriers. Examples of suitable carriers are well known in the art and may include, but are not limited to, any of the standard pharmaceutical carriers such as a phosphate buffered saline solutions phosphate buffered saline containing Polysorb 80, water, emulsions such as oilwater emulsion, and various type of wetting agents. Other carrier may also include sterile solutions, tablets, coated tablets, and capsules.

Typically such carriers contain excipients such as starch, milk, sugar, certain types of clay gelatin, stearic acid or salts thereof, magnesium or calcium stearate, talc, vegetable fats or oils, gums glycols, or other known excipients. Such carriers may also include flavor and color additives or other ingredients. Compositions comprising such carriers are formulated by well known convention methods.

Methods of determining an "effective amount" are well known to those skilled in the art and depend upon factors including, but not limited to: the size of the patient and the carrier used.

The invention is further defined by reference to the following examples and preparations which describe the manner and process of making and using the invention and are illustrative rather than limiting. It will be apparent to those skilled in the art that many modifications, both to the materials and methods, may be practiced without departing from the purpose and interest of the invention.

EXAMPLES

Example 1

Large-Scale Preparations of Trimbromosiloxy (TBSO) Protected Mono-Bromide as a Starting Material for Synthesis of Tubulin Binding Agents The following reactions are illustrated in FIG. 1:

3-tert-butyldimethylsiloxy (TBSO)-4-methoxybenzaldehyde (1).

To a 1-L round-bottom flask was added Isovanillin (80 g, 526 mol) and DMAP (1 g) under inert atmosphere. Dry dichloromethane (~450 mL) was added, followed by triethylamine (81 mL, 580 mol), at which point the solid entirely dissolved. The mixture was cooled to 0° C. and tert-butyldimethylsilyl ("TBS") chloride ("TBSCl", 89 g, 590 mol) was added in one portion. The mixture began almost immediately to precipitate solid. The mixture was allowed to stir for 1.5 h at 0° C., at which point TLC (30% EtOAc/hexanes) showed an almost complete absence of isovanillin. The mixture was allowed to stir overnight, then the precipitate was filtered off through Celite. The filtrate was washed with water (200 mL) followed by saturated NaCl solution (200 mL) and dried over MgSO4. This was filtered into a tared 1-L flask and concentrated by distillation on a rotary evaporator, followed by aspirator vacuum to approximately constant weight, yielding a deep red-brown liquid (149.4 g; theoretical=140 g). This material was taken into the next reaction without further characterization.

1-(3-tert-butyldimethylsiloxy(TBSO)-4-methoxyphenyl) ethanol (2).

The entire crude product from the preceding reaction (~526 mol) was transferred as a solution in dry ether (200 mL) to a 2-L round bottom flask equipped with a very large magnetic stirring bar. An additional 500 mL of dry ether were added and the mixture was cooled to 0° C. Then methyllithium (500 mL of a 1.4 M solution, 700 mol) was added over ~40 minutes by cannula, and the mixture was allowed to stir overnight. The deep red mixture was recooled to 0° C. and treated with water (200 mL) very cautiously at first. The mixture became a heterogeneous yellow. In a separatory funnel, the aqueous phase was separated and the organic phase was washed once with saturated NaCl solution and dried over MgSO4. After filtration and concentration by distillation on a rotary evaporator followed by aspirator vacuum, a deep red liquid was obtained (136.8 g), and was found to be free of starting material by TLC. This material was taken into the next reaction without further characterization.

3-tert-butyldimethylsiloxy(TBSO)-4-methoxyacetophenone (3).

The entire amount of the crude alcohol from the preceding reaction was transferred to a 3-L round bottom flask as a solution in ~1.5 L of dry dichloromethane. Celite (62 g, oven dried), $K_2CO_3$ (16 g) and a very large magnetic stirring bar were added. PCC (115 g) was then added in portions over a 2-hr period, during which time the heterogeneous yellow mixture became dark brown. At the end of the addition, large amounts of the starting alcohol were still present by TLC (25% EtOAc/hexanes) so the mixture was allowed to stir overnight. At this point, the starting alcohol was absent (or nearly so) by TLC, and the mixture was filtered through a 3-cm pad of silica gel, rinsing well with dichloromethane. The mud-brown solution was concentrated by distillation on a rotary evaporator followed by aspirator vacuum to yield an opaque brown liquid. This was purified in 30 mL portions by Kugelrohr distillation (~0.5 Torr, 140° C.) to yield 104.4 g of a brown liquid which crystallized on brief standing. This was dissolved in hot hexanes (104 mL) and filtered hot through Celite to yield a clear yellow solution. This was seeded and left in a refrigerator (~5° C.) overnight. The crystalline product was filtered cold, washed quickly with a small amount of cold hexanes and dried under pump vacuum to give 84.8 g (303 mol, 58% yield from isovanillin) recrystallized light yellow solid, pure by $^1H$ and $^{13}C$ NMR. A second crop of crystals (6.3 g) were obtained by dissolving the concentrated filtrate in hot hexanes (20 mL) followed by seeding and standing overnight.

3. $^1H$ NMR ($CDCl_3$): 0.15 (s, 6H); 0.98 (s, 9H); 2.52 (s, 3H); 3.85 (s, 3H); 6.85 (dd, 1H, J=8.4); 7.45 (s, 1H); 7.56 (dd, 1H, J=8.4, 2.2).

$^{13}C$ NMR ($CDCl_3$): −4.8, 18.4, 25.6, 26.3, 55.4, 110.7, 120.2, 123.5, 130.5, 144.7, 155.3, 196.8.

α-halo-3-tert-butyldimethylsiloxy(TBSO)-4-methoxyacetophenone (5)

An important part of the present invention is a new efficient method of converting 3-TBSO-4-methoxyacetophenone (3) to α-halo-3-TBSO-4-methoxyacetophenone (5) by treatment of the trimethylsilyl enol ether (4) [1-(3-TBSO-4-methoxyphenyl)-1-trimethylsiloxy(TMSO)-ethylene] with elemental halogen. Bromine is the preferred halogen. It is understood that chlorine and iodine may be utilized in place of bromine should iodo or chloro analogs be desired.

Example 2

Synthesis of Substituted Tetralones

Figure 8:
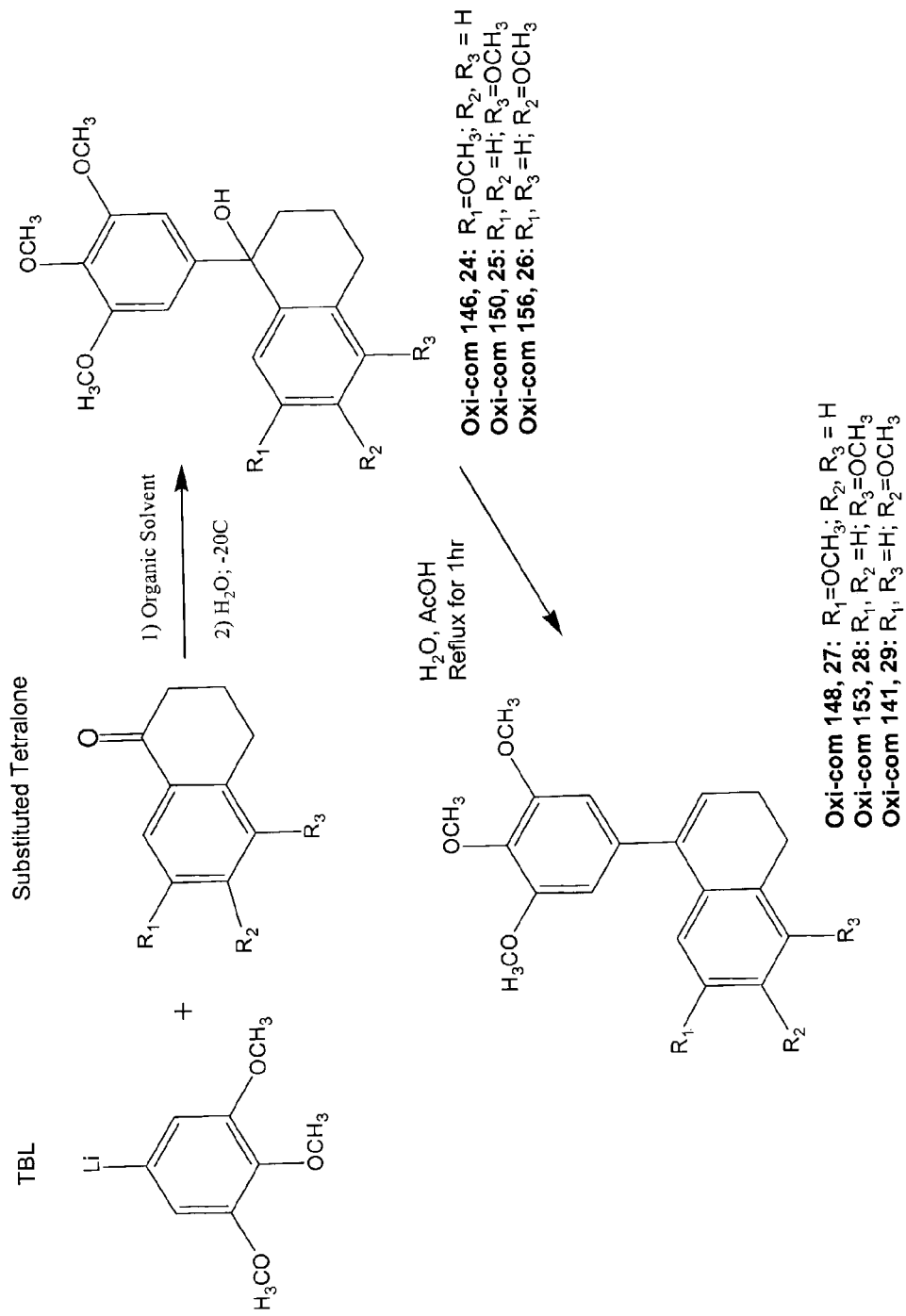
FIG. 8 illustrates a general synthetic route for the preparation of aryl-substituted dihydronaphthalene tubulin binding agents.

A fundamental intermediate in the synthesis of the compounds of the present invention is a substituted tetralone structure (see FIG. 8).

a. Synthesis of Mono-Hydroxy Substituted Tetralone

Figure 2:
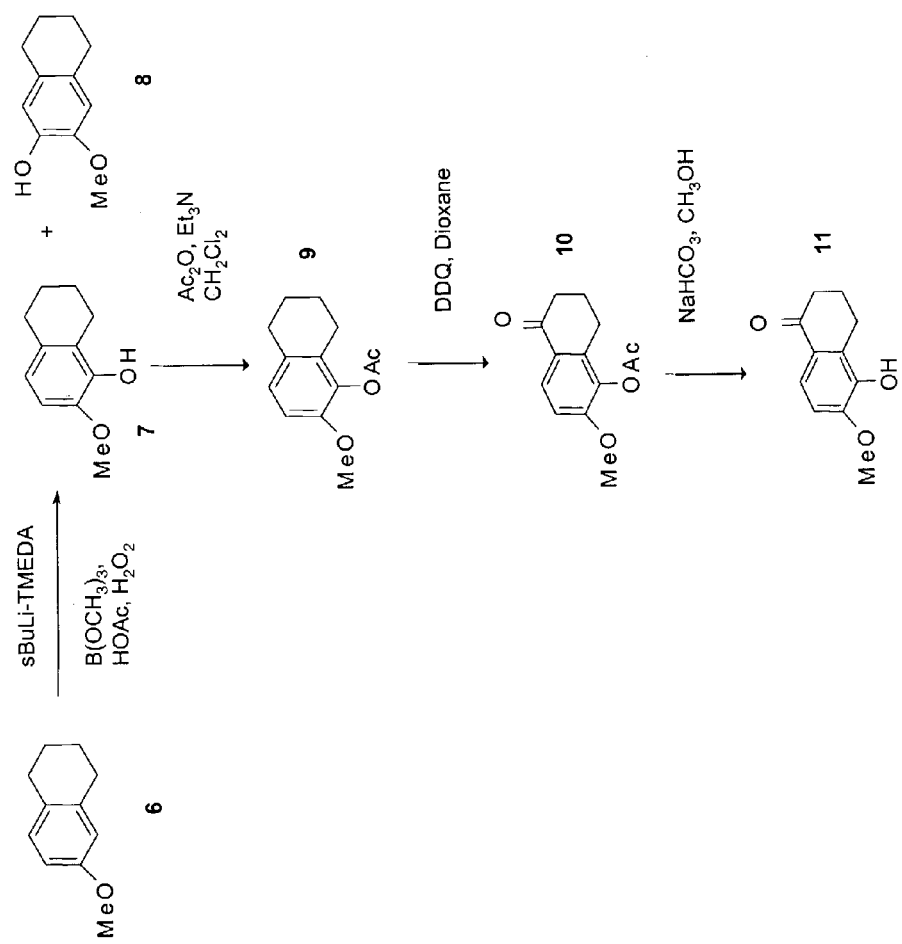
FIG. 2 illustrates a synthetic route for the preparation of an exemplary hydroxyl-substituted tetralone.

A procedure for the synthesis of mono-hydroxy substituted tetralone from tetrahydronaphthalene is illustrated with an exemplary synthetic route in FIG. 2. A mixture of 6-methoxy-1,2,3,4-tetrahydronaphthalene (6) and TMEDA was treated with sec-butyllithium at room temperature followed by addition of trimethyl borate. The resultant mixture was subsequently treated with acetic acid and 35% hydrogen peroxide to form the hydroxytetrahydronaphthalenes 7 and 8 which are easily separated by column chromatography.

The 5-hydroxy isomer 7 was converted to 5-acetoxy-6-methoxy-1,2,3,4-tetrahydronaphthalene (9) in 95% yield. Reaction of the 9 with DDQ in dioxane-water led to the formation of tetralone 10 as a single isomer in 96% yield. The correct position of the keto group was confirmed by single-crystal X-ray crystallography. The acetate was removed by treating tetralone 10 with sodium bicarbonate in methanol to form 5-hydroxy-6-methoxy-1-tetralone (11).

5-Hydroxy-6-methoxy-1-tetralone (11): $^1H$-NMR (300 MHz, $CDCl_3$) δ 2.11 (m, 2H), 2.60 (t, 2H, J=6.2 Hz), 2.93 (t, 2H, J=6.1 Hz), 3.95 (s, 3H), 5.75 (bs, 1H), 6.83 (d, 1H, J=8.6 Hz), 7.68 (d, 1H, J=8.6 Hz).

b. Synthesis of Dihydroxy-Substituted Tetralones

Figure 3:
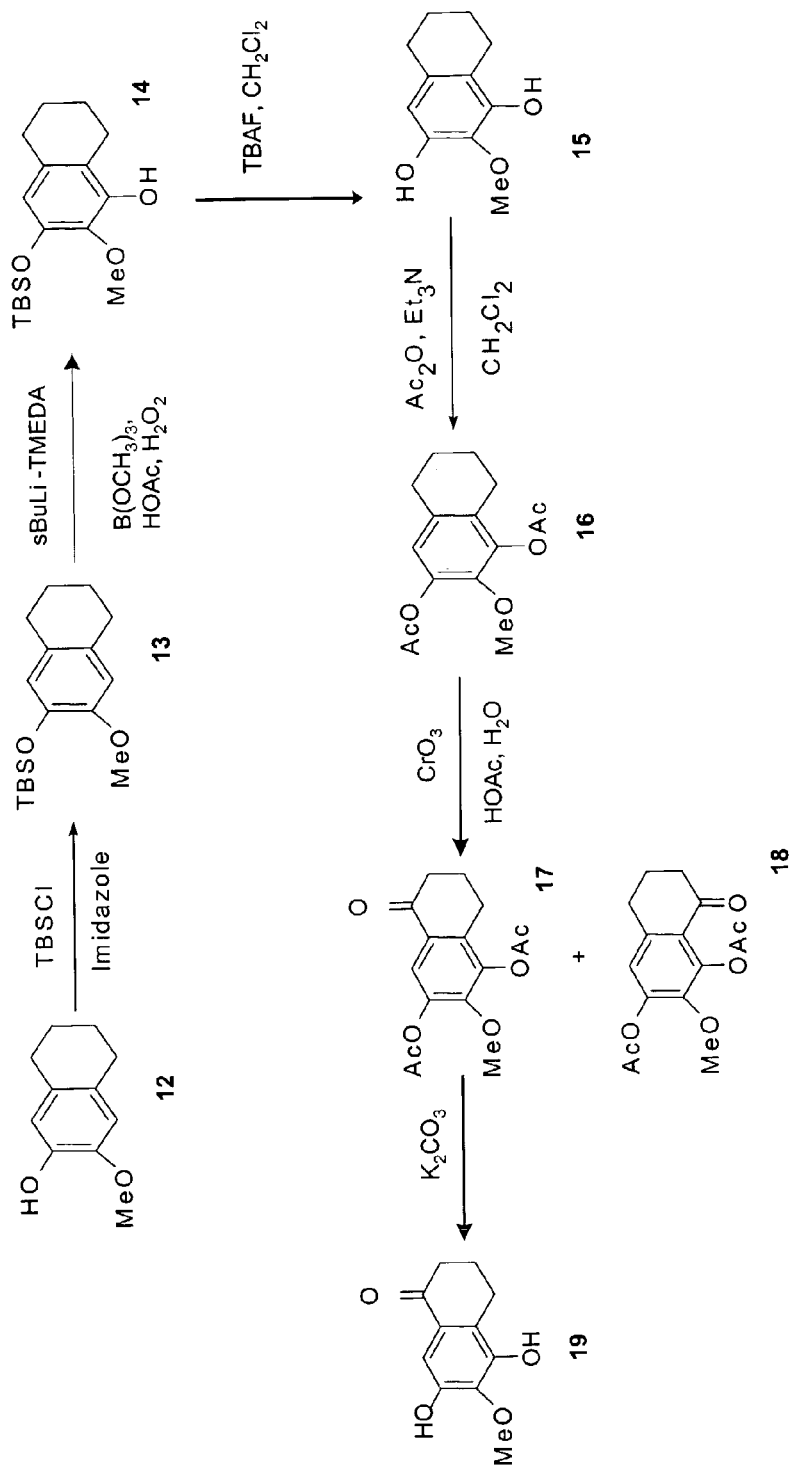
FIG. 3 illustrates a synthetic route for the preparation of an exemplary dihydroxy-substituted tetralone.

In order to synthesize dihydroxy-substituted dihydronaphthalenes and their corresponding prodrugs, the invention provides the synthesis di-hydroxytetralones as intermediates. The synthesis of an exemplary dihydroxy tetralone is provided in FIG. 3. 5,7-dihydroxy-6-methoxy-1-tetralone (19) is synthesized by protection of the 7-hydroxy group in the tetrahydronaphthalene 17 as its corresponding TBS ether (13) proceeded in high yield. In regard to regioselective introduction of the hydroxy group, we anticipated that due to different ortho-directing effects of methoxy and -OTBS groups, it should prove possible to obtain one of the isomers in much higher amount over the other. Accordingly, when tetrahydronaphthalene 13 was treated sequentially with sec-butyllithium-TMEDA, trimethylborate, acetic acid, and 35% hydrogen peroxide, and 5-hydroxy-6-methoxy-7-(tert-butyldimethylsiloxy)-1,2,3,4-tetrahydronaphthalene (14) was obtained as a single product. The TBS protecting group was removed by treating tetrahydronaphthalene 14 with 1M TBAF in THF and the two hydroxy groups of the resultant tetrahydronaphthalene 15 were converted to the corresponding acetates to give 5,7-diacetoxy-6-methoxy-1,2,3,4-tetrahydronaphthalene (16). Unfortunately, all of our efforts to convert the tetrahydronaphthalene 16 to the corresponding tetralone failed using DDQ under various conditions. In order to overcome the problem of oxidation, we considered different oxidizing agents. After various trials, chromium (VI) oxide in acetic acid-water was found to be the reagent of choice. Thus, tetrahydronaphthalene 16 was converted to 5,7-diacetoxy-6-methoxy-1-tetralone (17) in 54% yield. Approximately 5% of isomeric tetralone 18 was also formed. Again in this case, the para-directing effect of the methoxy group led to the formation of the tetralone 17 predominantly. The acetates in tetralone 17 were removed by treatment with potassium carbonate in methanol to produce 5,7-dihydroxy-6-methoxy-1-tetralone (19).

5,7-Diacetoxy-6-methoxy-1-tetralone (19): $^1$H-NMR (300 MHz, CDCl$_3$) δ 2.08–2.14 (m, 2H), 2.32 (s, 3H), 2.36 (s, 3H), 2.61 (t, 2H, J=6.6 Hz), 2.74 (t, 2H, J=6.0 Hz), 7.69 (s, 1H).

c. Synthesis of Amino-Functionalized Tetralones

6-Methoxy-5-Nitro-1-Tetralone and 6-Methoxy-7-Nitro-1-Tetralone

Figure 4:
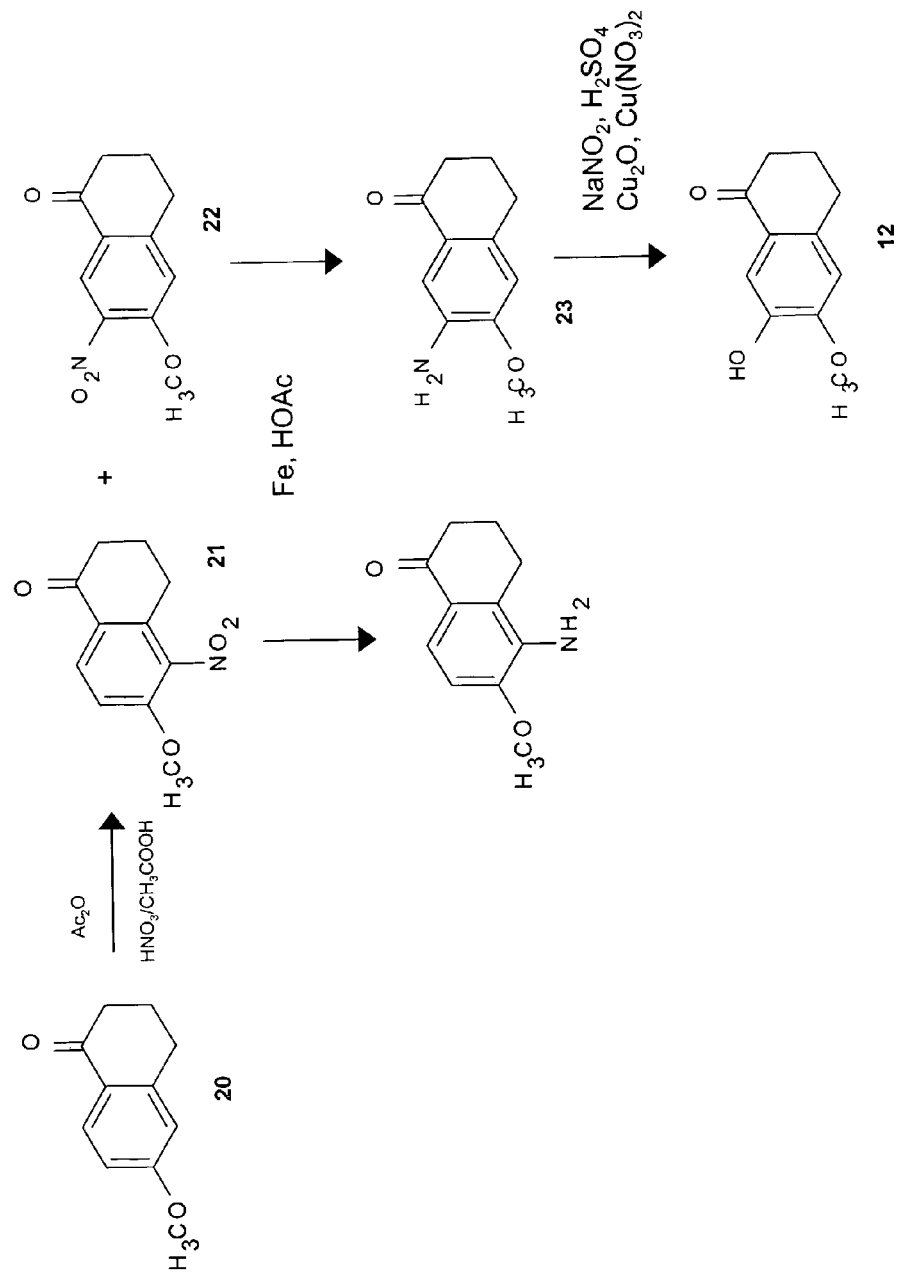
FIG. 4 illustrates a synthetic route for the preparation of exemplary amine-substituted tetralones.

A procedure for the synthesis of mono-amino substituted tetralone from tetrahydronaphthalene is illustrated with an exemplary synthetic route in FIG. 4. To an ice-cold, stirred solution of 6-methoxy-1-tetralone (20, 17.6 g, 0.10 mol) in acetone (30 mL) was added dropwise a mixture of sulfuric acid (18 mL, 96.0%) and nitric acid (15 mL, 68.0–70.0%). After the addition was complete, the reaction was stirred at 0° C. for 6 hours, and TLC was employed to monitor the reaction progress. The reaction mixture was poured into ice-water, and the mixture was partitioned between CH$_2$Cl$_2$ (3×200 mL) and water (200 mL). The organic layer was washed by saturated NaHCO$_3$ solution and water (200 mL each), dried over anhydrous sodium sulfate, and, after filtration, the organic layer was concentrated in vacuo to provide a yellow oil. 6-Methoxy-5-nitro-1-tetralone (21, 7.74 g, 0.035 mol) and 6-methoxy-7-nitro-1-tetralone (22, 6.63 g, 0.030 mol) were obtained after purification by column chromatography:

6-Methoxy-5-nitro-1-tetralone (21): $^1$H-NMR (CDCl3, 300 MHz) δ 2.15 (m, 2H), 2.65 (t, J=6.2 Hz, 2H), 2.87 (t, J=6.0 Hz, 2H), 7.02 (d, J=8.7 Hz, 1H), 8.19 (d, J=8.9 Hz, 1H).

6-Methoxy-7-nitro-1-tetralone (22): $^1$H-NMR (CDCl$_3$, 300 MHz) δ 2.15 (m, 2H), 2.67 (t, J=6.2 Hz, 2H), 3.01 (t, J=6.1 Hz, 2H), 6.90 (s, 1H), 8.52 (s, 1H).

To a solution of acetic acid (20 mL) in H$_2$O (100 mL), 7-nitro-6-methoxy-1-tetralone (21) (2.21 g, 10.0 mol) was added. The solution was heated to reflux for 1 hour, and then cooled down to RT. NaHCO$_3$ (60 mL, saturated solution) was added, and the mixture was partitioned between CH$_2$Cl$_2$ and water. The organic layer was dried over anhydrous sodium sulfate. After filtration, the organic layer was concentrated in vacuo to provide (23) as a red oil.

7-Amino-6-methoxy-1-tetralone (23): (1.74 g, 9.1 mol, 91%) $^1$H-NMR (CDCl$_3$, 300 MHz) 2.07 (m, 2H), 2.57 (t, J=6.5 Hz, 2H), 2.86 (t, J=6.0 Hz, 2H), 3.73 (b, 2H), 3.91 (s, 3H), 6.59 (s, 1H), 7.36 (s, 1H).

Hydroxy-functionalized tetralones were also obtained from amino-functionalized counterpart. For example, 23 (0.96 g, 5.0 mol) was dissolved in a mixture of sulfuric acid (96%, 2.1 mL) and H$_2$O (3.9 mL). The solution was cooled to 0° C., and ice (5.0 g) was added resulting in the crystallization of a solid. A solution of NaNO$_2$ (0.48 g, 7 mol) in H$_2$O (5 mL) was added dropwise at 0° C., After the solution had been stirred for an additional 10 min, a few crystals of urea were added to decompose any excess sodium nitrite. To the cold solution of benzenediazonium bisulfate was added a solution of cupric nitrate trihydrate (19.0 g, 78.6 mol) in H$_2$O (150 mL) at 0° C. With vigorous stirring, cuprous oxide (0.72 g, 5.0 mol) was added to the solution. The solution was stirred for 10 more min, and TLC was employed to monitor the reaction. The mixture was partitioned between ethyl ether and water. The organic layer was dried over anhydrous sodium sulfate, and after filtration, the organic layer was concentrated in vacuo to provide (12) as a yellow oil.

7-Hydroxy-6-methoxy-1-tetralone (12): (0.22 g, 1.15 mol, 23%) $^1$H-NMR (CDCl$_3$, 300 MHz) 2.09 (m, 2H), 2.59 (t, J=6.5 Hz, 2H), 2.88 (t, J=6.0 Hz, 2H), 3.95 (s, 3H), 5.60 (s, 1H), 6.66 (s, 1H), 7.56 (s, 1H). $^{13}$C-NMR (CDCl$_3$, 75 MHz) 23.6, 29.5, 38.6, 56.0, 109.6, 112.2, 126.5, 138.4, 144.4, 151.0, 197.2.

Example 3

Aryl Substituted Dihydronaphthalene-Based Tubulin Binding Agents

Figure 5A:
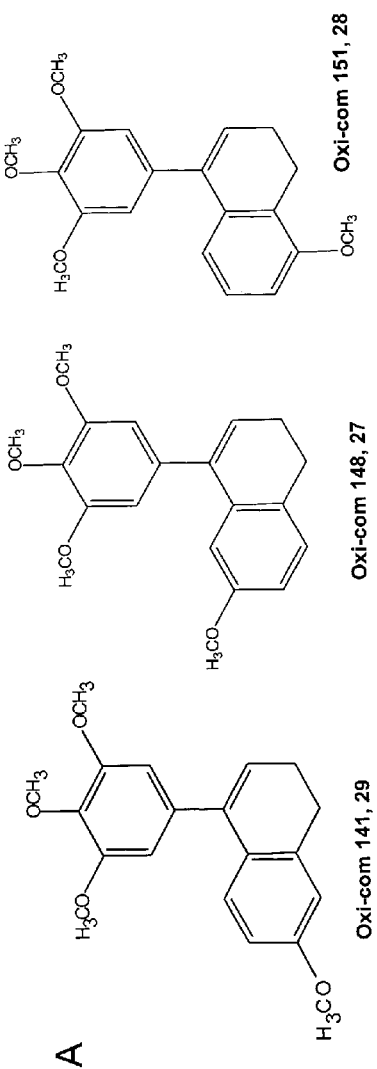
FIG. 5A) depicts exemplary aryl-substituted dihydronaphthalene tubulin binding agents and; B) amine, aryl-substituted dihydronaphthalene tubulin binding agents and corresponding prodrug constructs FIG. 6A) depicts exemplary hydroxyl, aryl-substituted dihydronaphthalene tubulin binding agents and; B) corresponding prodrug constructs.

Our interest in preparing the following aryl-substituted dihydronaphthalene ligands was based on our molecular recognition studies which suggest an optimal aryl-aryl distance (centroid to centroid) for enhanced tubulin binding. Exemplary aryl-substituted dihydronapthalene ligands are depicted in FIG. 5A.

Each aryl-substituted compound was synthesized according the generalized synthetic scheme illustrated in FIG. 8.

a. Synthesis of Aryl-Substituted Tetrahydronaphthalen-1-ol

To a stirred solution of n-butyllithium (3.7 mL, 1.6 M in hexane solution, 6.0 mol) in dry ether (40 mL), a solution of 3,4,5-trimethoxyphenylbromide (0.74 g, 3.0 mol) in ether (20 mL) was added under dry nitrogen at −78° C. The solution was stirred for 1 h in order to form 3,4,5-trimethoxyphenyllithum ("TPL"). Substituted tetralone reagent (3.0 mol) was added at −20° C., and the stirring was continued for 2 h (−20° C.—RT). The mixture was partitioned between CH$_2$Cl$_2$ and water, the organic layer was dried over anhydrous sodium sulfate, and, after filtration, the organic layer was concentrated in vacuo to provide a tetrahydronaphthalen-1-ol as a yellow oil. Each compound was purified by column chromatography.

Oxi-com 146 (24) (61% yield) $^1$H-NMR (CDCl$_3$, 300 MHz) δ 1.82 (m, 1H), 1.96 (m, 1H), 2.10 (t, J=5.7 Hz, 2H), 2.82 (t, J=5.9 Hz, 2H), 3.68 (s, 3H), 3.78 (s, 6H), 3.85 (s, 3H), 6.55 (s, 2H), 6.22 (d, J=2.6 Hz, 1H), 6.80 (dd, J=2.7, 8.4 Hz, 1H), 7.08 (d, J=8.4 Hz, 1H). $^{13}$C-NMR (CDCl$_3$, 75 MHz) δ 14.1, 19.8, 28.9, 41.3, 55.3, 56.1, 60.8, 75.7, 103.8, 113.0, 114.3, 129.7, 129.9, 136.5, 142.6, 144.4, 152.5, 157.9. HRMS (EI) M$^+$, calcd for C$_{20}$H$_{24}$O$_5$ 344.1624, found 344.1622.

Oxi-com 150 (25) (41% yield) $^1$H-NMR (CDCl$_3$, 300 MHz) δ 1.84 (m, 1H), 2.00 (m, 1H), 2.12 (m, 2H), 2.22 (s, 1H), 2.67 (m, 1H), 2.94 (m, 1H), 3.78 (s, 6H), 3.85 (s, 3H), 3.87 (s, 3H), 6.55 (s, 2H), 6.70 (d, J=8.0 Hz, 1H), 6.77 (d, J=8.1 Hz, 1H), 7.13 (t, J=7.9 Hz, 1H). $^{13}$C-NMR (CDCl$_3$, 75 MHz) δ 19.2, 23.6, 41.0, 55.7, 56.4, 61.1, 75.8, 104.1, 108.8, 120.9, 126.9, 127.1, 136.7, 143.0, 145.0, 152.8, 157.0. HRMS (EI) M$^+$, calcd for C$_{20}$H$_{24}$O$_5$ 344.1624, found 344.1622.

Oxi-com 156 (26) (58% yield) $^1$H-NMR (CDCl$_3$, 300 MHz) δ 1.82 (m, 1H), 2.00 (m, 4H) 2.88 (t, J=6.2, 2H), 3.79

(s, 6H), 3.80 (s, 3H), 3.85 (s, 3H), 6.57 (s, 2H), 6.69 (m, 2H), 6.99 (d, J=7.5 Hz, 1H). $^{13}$C-NMR (CDCl$_3$, 75 MHz) δ 19.7, 30.2, 41.4, 55.2, 56.1, 60.8, 75.2, 103.7, 112.8, 112.9, 130.2, 134.1, 136.4, 139.1, 144.9, 152.5, 158.7. HRMS (EI) M$^+$, calcd for C$_{20}$H$_{24}$O$_5$ 344.1624, found 344.1626.

b. Synthesis of Aryl-Substituted Dihydronaphthalenes. To a solution of acetic acid (10 mL) in H$_2$O (60 mL), compounds 24, 25, 26, (1 mol) were added respectively. The solution was heated to reflux for 1 hour, and then cooled down to RT. NaHCO$_3$ (20 mL, saturated solution) was added, and the mixture was partitioned between CH$_2$Cl$_2$ and water. The organic layer was dried over anhydrous sodium sulfate, after filtration, the organic layer was concentrated in vacuo to provide the following compounds as a yellow oil. Each compound compound was purified by column chromatography.

Oxi-com 148 (27) (92% yield) $^1$H-NMR (CDCl$_3$, 300 MHz) δ 2.83 (m, 2H), 2.79 (t, J=7.7 Hz, 2H), 3.71 (s, 3H), 3.85 (s, 6H), 3.89 (s, 3H), 6.11 (t, J=4.6 Hz, 1H). 6.57 (s, 2H), 6.65 (d, J=2.6 Hz, 1H), 6.73 (dd, J=2.6, 8.2 Hz, 1H), 7.13 (d, J=8.2 Hz, 1H). $^{13}$C-NMR (CDCl$_3$, 75 MHz) δ 24.1, 27.6, 55.7, 56.4, 61.3, 106.0, 112.0, 112.3, 128.4, 128.5, 129.2, 136.3, 136.7, 137.3, 140.1, 153.3, 158.4. HRMS (EI) M$^+$, calcd for C$_{20}$H$_{22}$O$_4$ 326.1518, found 326.1507. Anal. Calcd for C$_{20}$H$_{22}$O$_4$: C, 73.60; H, 6.79. Found: C, 73.77; H, 6.93.

Oxi-com 153 (28) (90% yield) $^1$H-NMR (CDCl$_3$, 300 MHz) δ 2.39 (m, 2H), 2.86 (t, J=8.3 Hz, 2H), 3.84 (s, 6H), 3.87 (s, 3H), 3.89 (s, 3H), 6.10 (t, J=4.6 Hz, 1H), 6.55 (s, 2H), 6.71 (d, J=7.7 Hz, 1H), 6.82 (d, J=8.2 Hz, 1H), 7.11 (t, J=8.1 Hz, 1H). 13C-NMR (CDCl$_3$, 75 MHz) δ 19.8, 22.8, 55.6, 56.1, 60.9, 105.7, 109.7, 118.5, 124.5, 126.2, 127.7, 136.0, 136.8, 136.9, 139.7, 152.8, 156.0. HRMS (EI) M$^+$, calcd for C$_{20}$H$_{22}$O$_4$ 326.1518, found 326.1518. Anal. Calcd for C$_{20}$H$_{22}$O$_4$: C, 73.60; H, 6.79. Found: C, 73.77; H, 6.84.

Oxi-com 141 (29) (90% yield) $^1$H-NMR (CDCl$_3$, 300 MHz) δ 2.83 (m, 2H), 2.83 (t, J=7.6 Hz, 2H), 3.82 (s, 3H), 3.85 (s, 6H), 3.89 (s, 3H), 5.95 (t, J=4.5 Hz, 1H), 6.56 (s, 2H), 6.66 (dd, J=2.6, 8.4 Hz, 1H), 6.73 (d, J=2.6 Hz, 1H), 7.00 (d, J=8.4 Hz, 1H). $^{13}$C-NMR (CDCl$_3$, 75 MHz) δ 23.8 29.2, 55.7, 56.5, 61.4, 106.1, 111.2, 114.2, 125.2, 127.1, 128.5, 137.1, 137.4, 139.0, 139.9, 153.4, 159.0. HRMS (EI) M$^+$, calcd for C$_{20}$H$_{22}$O$_4$ 326.1518, found 326.1515.

Example 4

Figure 5B:
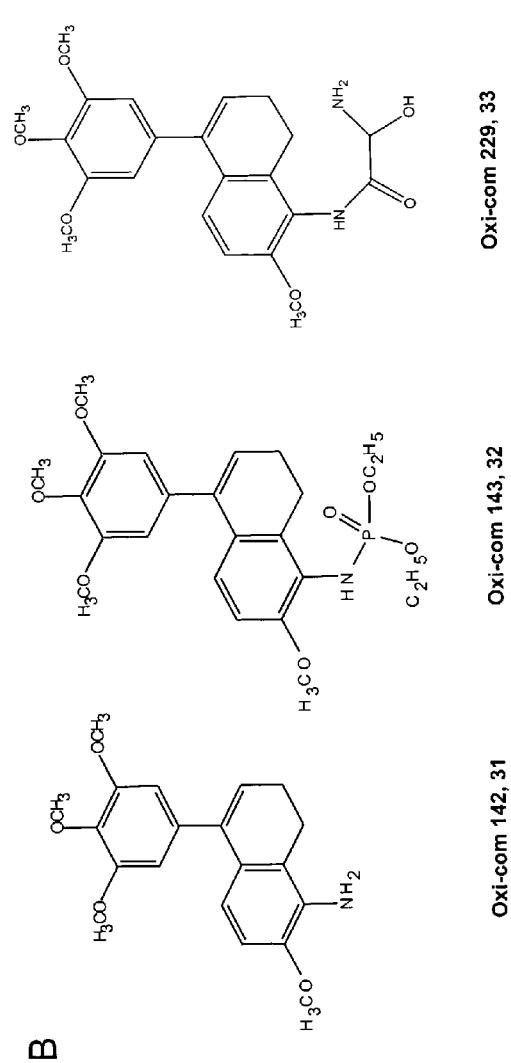
Figure 9:
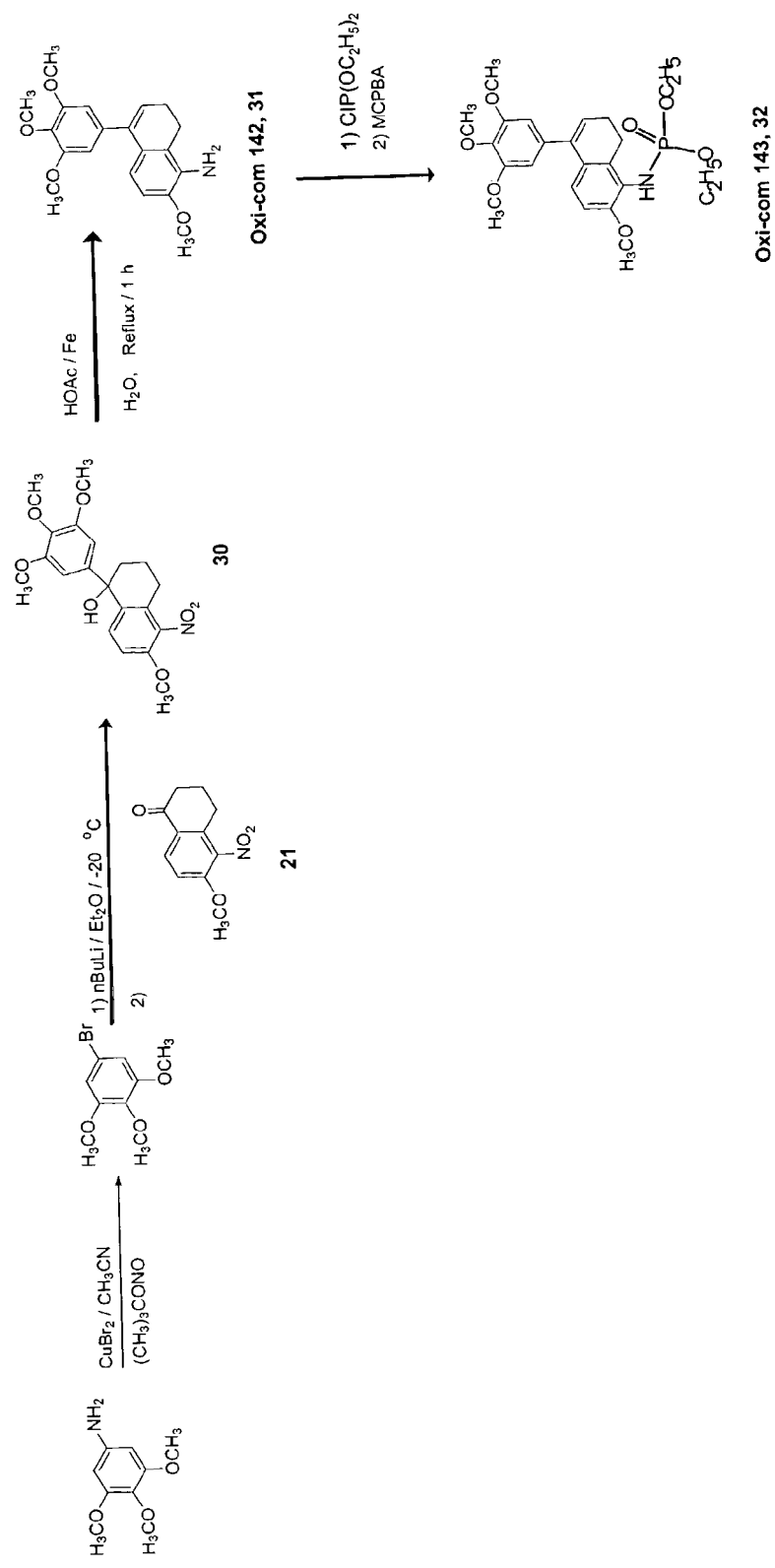
FIG. 9 illustrates a synthetic route for the preparation of an exemplary amine, aryl-substituted dihydronaphthalene and its corresponding phosphoramidate prodrug.

Synthesis of a Functionalized Aryl and Aroyl-Substituted Dihydronaphthalene-Based Tubulin Binding Agents and Corresponding Prodrugs a) Synthesis of Amino, Aryl-Substituted Dihydronapthalene Analogs Amine, Aryl-substituted dihydronaphthelene compounds and their corresponding prodrugs are contemplated as part of the invention. Exemplary compounds are depicted in FIG. 5. The C-5 amine dihydronapthalene derivative, Oxi-com 142 (31), and its phosphoramidate prodrug Oxi-com 143 (32) were synthesized as illustrated in FIG. 9.

To a stirred solution of n-butyllithium (15.0 mL, 1.6 M in hexane solution, 24.0 mol) in dry ether (160 mL), a solution of 3,4,5-trimethoxyphenylbromide (2.97 g, 12.0 mol) in ether (40 mL) was added under dry nitrogen at −78° C. The solution was stirred for 1 h in order to form 3,4,5-trimethoxyphenyllithum.

6-Methoxy-5-nitro-1-tetralone (21) (2.65 g, 12.0 mol) was added at −20° C. to the trimethoxyphenyllithium and stirring was continued for 2 h (−20° C. -RT). The mixture was partitioned between CH$_2$Cl$_2$ and water, the organic layer was dried over anhydrous sodium sulfate, and, after filtration, the organic layer was concentrated in vacuo, to afford 1-Hydroxy-6-methoxy-5-nitro-1-(3',4',5'-trimethoxyphenyl) tetralin (30) as a crude yellow oil. (GC-MS shows the yield is about 55%). This compound, without purification, was added to a refluxing mixture of acetic acid (10 mL) and water (80 mL), and iron (0.5 g) was added. After heating at reflux for 1 h, the mixture was partitioned between CH$_2$Cl$_2$ (3×100 mL) and water (100 mL). The organic layer was washed with NaHCO$_3$ (sat.) and water (100 mL each), dried over anhydrous sodium sulfate, and, after filtration, the organic layer was concentrated in vacuo to provide a yellow oil. Purification by column chromatography afforded 5-Amino-6-methoxy-1-(3',4',5'-trimethoxyphenyl)-3,4-dihydronaphthalene (31):

Oxi-com 142 (31) (2.03 g, 5.95 mol). $^1$H-NMR (CDCl$_3$, 300 MHz) δ 2.43 (m, 2H), 2.68 (t, J=7.8 Hz, 2H), 3.84 (s, 6H), 3.86 (s, 3H), 3.89 (s, 3H), 5.93 (t, J=4.7 Hz, 1H), 6.51 (d, J=8.4 Hz, 1H). 6.56 (s, 2H), 6.60 (d, J=8.4 Hz, 1H). $^{13}$C-NMR (CDCl$_3$, 75 MHz) δ 22.0, 23.3, 56.0, 56.5, 61.3, 106.4, 107.5, 117.2, 121.6, 124.5, 128.6, 132.8, 137.4, 137.6, 140.4, 147.5, 153.2. HRMS (EI) M$^+$, calcd for C$_{20}$H$_{23}$NO$_4$ 341.1627, found 341.1635. Anal. Calcd for C$_{20}$H$_{23}$NO$_4$: C, 70.36; H, 6.79; N: 4.10. Found: C, 70.24; H, 6.74; N, 4.08.

To a stirred solution of ClP(OC$_2$H$_5$)$_2$ (0.157 g, 1.0 mol) in dry ethyl ether (20 mL) was added slowly a solution of 31 (0.341 g, 1 mol) in dry ethyl ether (30 mL) at −78° C. Once this addition was complete, a solution of N, N-diisopropylethylamine (0.28 g, 2.2 mol) in dry ethyl ether (2 mL) was added. The solution was stirred at −78° C. for 2 hours, followed by stirring at RT for 10 hours. The solution was filtered and concentrated in vacuo to provide a yellow oil. The yellow oil was dissolved in dry CH$_2$Cl$_2$ (10 mL), then cooled to −40° C. A solution of MCPBA (0.28 g) in dry CH$_2$Cl$_2$ (10 mL) was added. After stirring at RT for 1 h, the organic layer was washed with saturated Na$_2$SO$_4$ solution and water (10 mL each), dried over anhydrous sodium sulfate, and, after filtration, the organic layer was concentrated in vacuo to provide a yellow oil. Purification by column chromatography afforded 6-methoxy-1-(3',4',5'-trimethoxyphenyl)-5-diethylphosphoramidate-3,4-dihydronapthalene (32):

Oxi-com 143 (32): (0.286 g, 0.60 mol). $^1$H-NMR (CDCl$^3$, 300 MHz) δ 1.33 (t, J=7.0 Hz, 6H), 2.75 (t, J=8.5 Hz, 2H), 3.21 (t, J=8.6 Hz, 2H), 3.82 (s, 3H), 3.84 (s, 6H), 3.92 (s, 3H), 4.11 (m, 4H), 6.46 (s, 2H), 6.50 (d, J=8.4 Hz, 1H), 6.57 (d, J=8.6 Hz, 1H). $^{13}$C-NMR (CDC$_{l3}$, 75 MHz) δ 16.2, 16.3, 24.8, 32.4, 55.6, 56.2, 61.0, 62.9, 63.0, 107.0, 107.6, 123.7, 124.7, 129.1, 131.4, 133.4, 134.8, 152.8, 153.1. $^{31}$P-NMR (CDCl$_3$, 300 MHz) δ 6.51. HRMS (EI) M$^+$, calcd for C$_{24}$H$_{32}$NPO$_7$477.1916, found 477.1928.

Acyl amino acid ester prodrugs of Amino, Aryl-Substituted Dihydronapthalene Analogs were also synthesized. The L-serinamide prodrug derivative of 31 was obtained by dissolving 3,4-dihydro-5-FMOC-L-serinamide-6-methoxy-1-(3',4',5'-trimethoxyphenyl) naphthalene (0.0435 g, 0.0679 mmol) in $CH_2Cl_2$ (1.2 mL) and $CH_3OH$ (1.2 mL). While stirring, NaOH (0.003 g, 0.000075 mmol) was added and allowed to react at room temperature for 16 h. After completion, extraction of the organic layer was accomplished with EtOAc, water, and saturated NaCl (100 mL each). The organic layer was dried with anhydrous sodium sulfate. Purification by preparative TLC and flash column chromatography (silica gel, 90:10 methylene chloride:methanol) afforded the desired serinamide product (33)

Oxi-com 229 (33): (0.010 g, 0.024 mmol, 36%) $^1$H-NMR ($CDCl_3$, 300 MHz) δ 2.30 (m, 2H) 2.70 (t, J=7.70 Hz, 2H), 3.77 (s, 3H), 3.82 (s, 6H), 3.89 (s, 3H), 4.00 (m, 3H), 5.98 (t, J=4.45 Hz, 1H), 6.57 (s, 2H), 6.67 (d, J=8.55 Hz, 1H), 6.98 (d, J=8.55 Hz, 1H) $^{13}$C-NMR ($CDCl_3$, 300 MHz) δ 23.0, 24.0, 55.8, 56.1, 60.9, 105.8, 107.7, 125.1, 128.8, 135.3, 136.7, 139.5, 152.8, 152.9 b) Synthesis of Hydroxy-Dihydronaphthalene Analogs

Figure 6A:
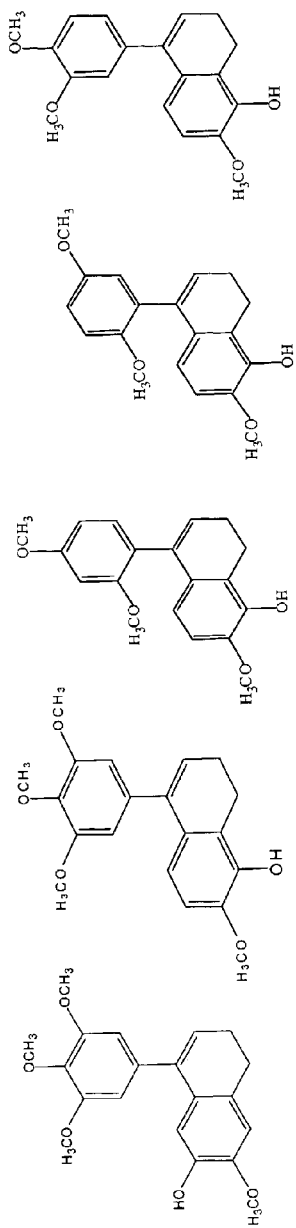
Figure 10:
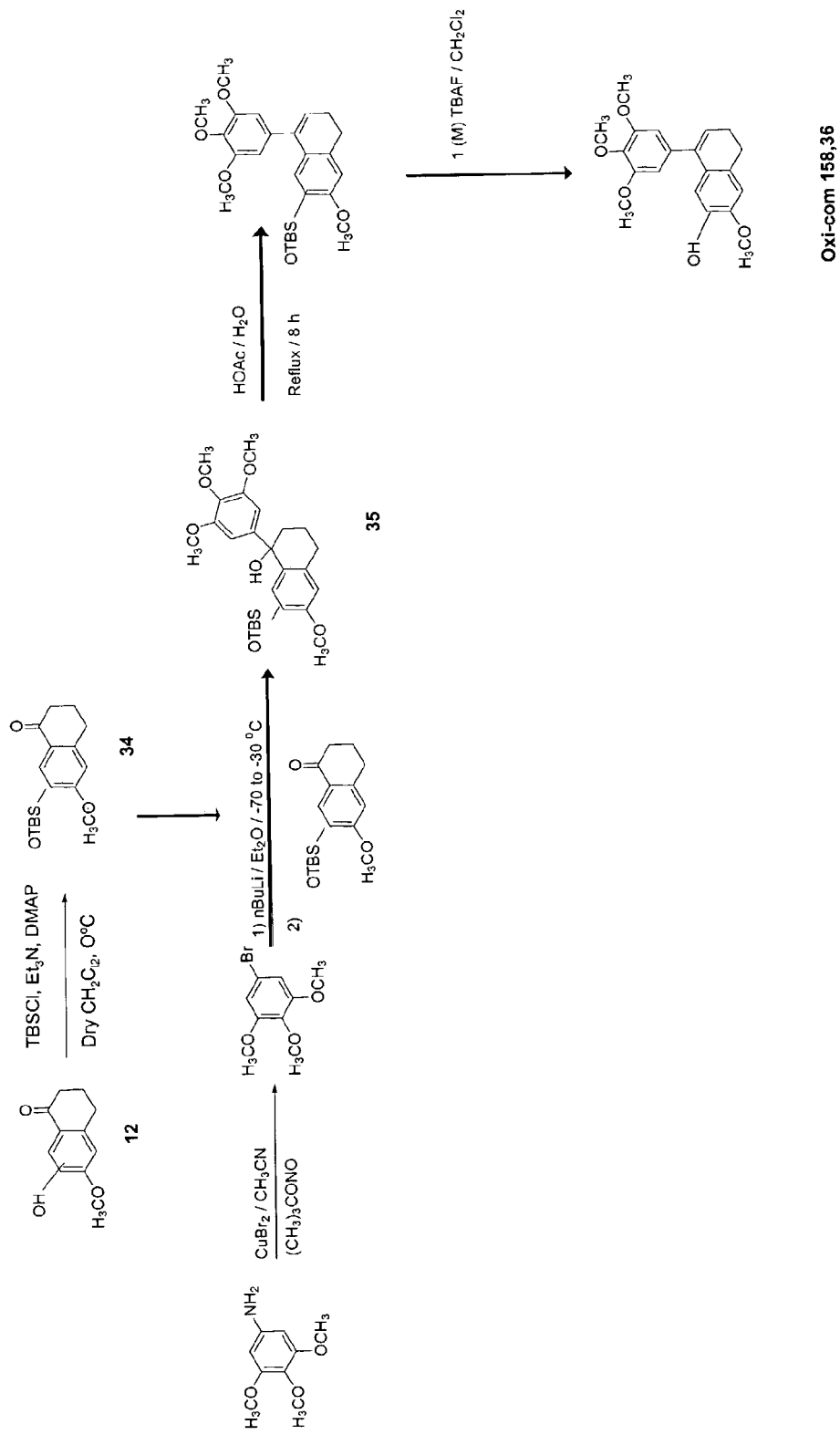
FIG. 10 illustrates a synthetic route for the preparation of an exemplary hydroxyl, aryl-substituted dihydronaphthalene tubulin binding agent.

Dihydronaphthalene compounds functionalized with hydroxy groups are contemplated in the present invention. Exemplary compounds are depicted in FIG. 6A. The exemplary C-7 hydroxy-dihydronaphthalene analog Oxi-com 158 (36) was synthesized based on the synthetic pathway illustrated in FIG. 10.

To a well-stirred solution of 7-Hydroxy-6-methoxy-1-tetralone (12, 80.0 mg, 0.42 mol) in $CH_2Cl_2$, was added $Et_3N$ (47 mg, 0.46 mol), followed by DMAP (5.1 mg, 0.042 mol) and TBSCl (69 mg, 0.46 mol) at 0° C. under dry nitrogen. After 2 h (at rt), the mixture was partitioned between $CH_2Cl_2$ and water. The organic layer was dried over anhydrous sodium sulfate, and after filtration, the organic layer was concentrated in vacuo to provide (34) as a yellow oil.

7-TBSO-6-methoxy-1-tetralone(34): (122 mg, 0.40 mol, 95%) $^1$H-NMR ($CDCl_3$, 300 MHz) 0.15 (s, 6H), 0.99 (s, 9H), 2.11 (m, 2H), 2.58 (t, J=6.1 Hz, 2H), 2.88 (t, J=6.0 Hz, 2H), 3.86 (s, 3H), 6.63 (s, 1H), 7.56 (s, 1H).

To a stirred solution of n-butyllithium (0.5 mL, 1.6 M in hexane solution, 0.80 mol) in dry ether (20 mL), a solution of 3,4,5-trimethoxyphenylbromide (98.8 mg, 0.40 mol) in ether (10 mL) was added under dry nitrogen at −78° C. The solution was stirred for 1 h in order to form 3,4,5-trimethoxyphenyllithium. 7-[(tertButyldimethylsilyl)oxy]-6-methoxy-1-tetralone (122 mg, 0.40 mol) was added at −20° C., and stirring was continued for 2 h (−20° C.—rt). The mixture was partitioned between $CH_2Cl_2$ and water, and the organic layer was dried over anhydrous sodium sulfate. After filtration, the organic layer was concentrated in vacuo to provide (35) as a yellow oil.

7-TBSO-1-hydroxy-6-methoxy-1-(3',4',5'-trimethoxyphenyl)-tetralone (35): (137 mg, 0.29 mol, 73%) $^1$H-NMR ($CDCl_3$, 300 MHz) 0.04 (s, 6H), 0.89 (s, 9H), 1.80 (b, 1H), 2.11 (m, 4H), 2.81 (t, J=6.5, 2H), 3.79 (s, 6H), 3.81 (s, 3H), 3.84 (s, 3H), 6.49 (s, 1H), 6.56 (s, 2H), 6.59 (s, 1H). $^{13}$C-NMR ($CDCl_3$, 75 MHz) −4.3, 18.8, 20.2, 26.1, 29.9, 41.5, 55.8, 56.5, 61.2, 75.6, 104.2, 111.9, 121.2, 131.4, 134.2, 136.8, 143.8, 145.3, 150.9, 152.9.

To a solution of acetic acid (10 mL) in $H_2O$ (60 mL), was added 7-TBSO-1-hydroxy-6-methoxy-1-(3',4',5'-trimethoxyphenyl)-tetralone (137 mg, 0.29 mol). The solution was heated to reflux for 8 hour, and then cooled down to RT. $NaHCO_3$ (20 mL, saturated solution) was added, and the mixture was partitioned between $CH_2Cl_2$ and water. The organic layer was dried over anhydrous sodium sulfate, and after filtration, the organic layer was concentrated in vacuo to provide 36 as a yellow oil.

Oxi-com 158 (36) (84.3 mg, 0.25 mol, 86%) $^1$H-NMR ($CDCl_3$, 300 MHz) 2.37 (m, 2H), 2.78 (t, J=7.7 Hz, 2H), 3.84 (s, 6H), 3.88 (s, 3H), 3.91 (s, 3H), 5.41 (s, 1H), 5.98 (t, J=4.6 Hz, 1H), 6.54 (s, 2H), 6.68 (s, 1H), 6.81 (s, 1H).

Figure 11:
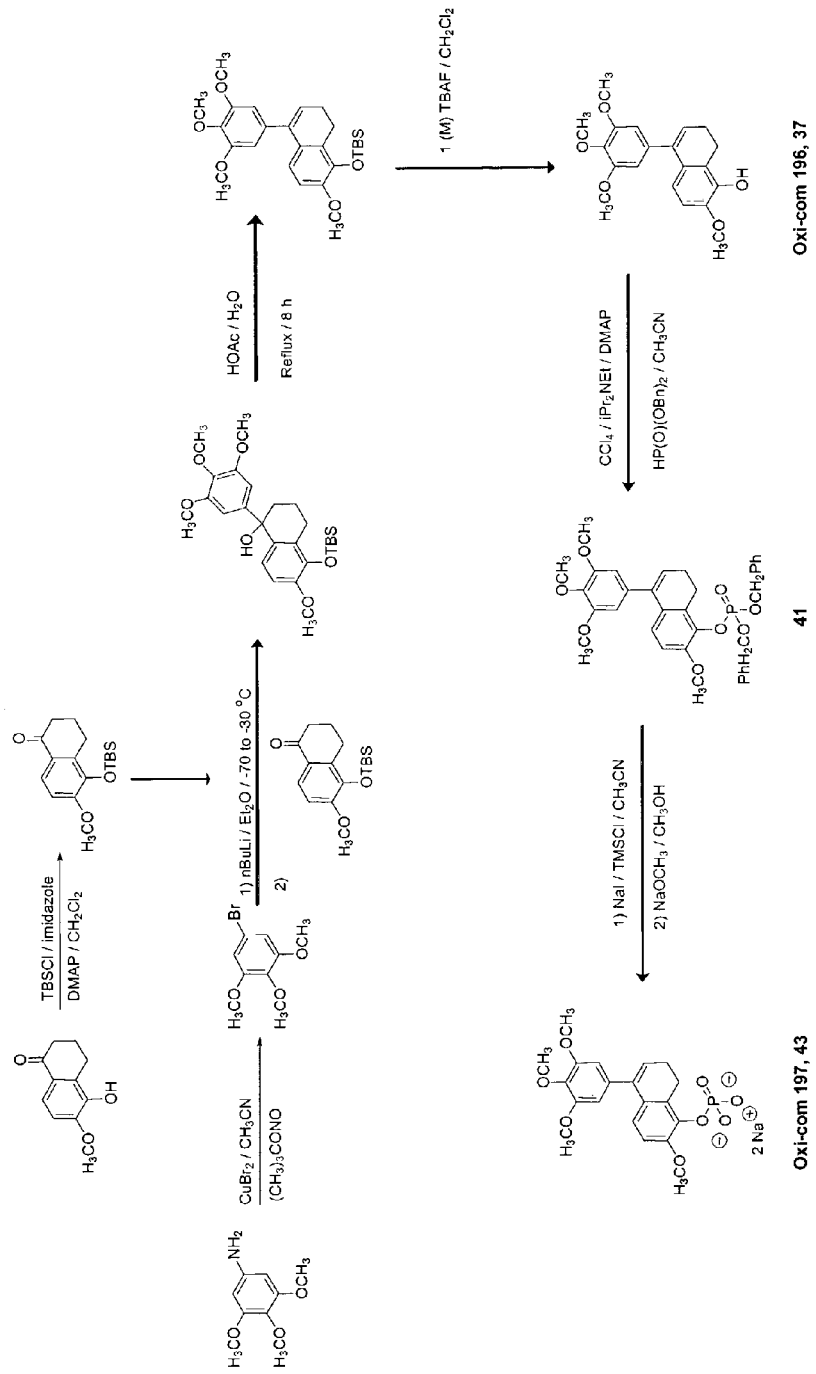
FIG. 11 illustrates a synthetic route for the preparation of an exemplary hydroxyl, aryl-substituted dihydronaphthalene tubulin binding agents and its corresponding phosphate prodrug.

Simliar dihydronaphthalenes functionalized in an analogous fashion at any other carbon position can readily be prepared. An exemplary detailed synthesis for the preparation of Oxi-com 196 is provided in FIG. 11.

Oxi-com 196 (37): $^1$H-NMR (300 MHz): δ 2.34–2.41(2H, m), 2.88 (2H, t, J=7.6 Hz), 3.84 (6H, s), 3.88 (6H, s), 5.72 (1H, s), 5.97 (1H, t, J=4.6 Hz), 6.55 (2H, s), 6.59 (1H, d, J=8.4 Hz), 6.63 (1H, d, J=8.4 Hz). $^{13}$C-NMR (75 MHz): δ 20.04, 22.62, 55.7, 55.87, 60.72, 105.63, 107.05, 117.21, 122.13, 125.18, 128.73, 136.72, 136.75, 139.32, 141.8, 145.68, 152.67.

Oxi-com 238 (38): $^1$H NMR ($CDCl_3$, 360 MHz): δ 7.08 (d, J=8.9 Hz, 1H), δ 6.53 (m, 3H), δ 6.26 (d, J=8.3 Hz, 1H), δ 5.86 (t, J=4.6 Hz, 1H), δ 5.67 (s, 1H), δ 3.84 (s, 6H), δ 3.68 (s, 3H), δ 2.91 (m, 2H), 2.4 (m, 2H).

Oxi-com 240 (39) $^1$H NMR ($CDCl_3$, 360 MHz): δ 6.81 (m, 3H), δ 6.55 (d, J=8.6 Hz, 1H), δ 6.27 (d, J=7.9 Hz, 1H), δ 5.9 (t, J=4.6 Hz, 1H), δ 5.67 (s, 1H), δ 3.85 (s, 3H), δ 3.77 (s, 3H), δ 3.65 (s, 3H), δ 2.92 (m, 2H), δ 2.41 (m, 2H).

Oxi-com 242 (40) $^1$H NMR ($CDCl_3$, 300 MHz): δ 6.88 (m, 3H), δ 6.62 (d, J=8.4 Hz, 1H), δ 6.57 (d, J=8.4 Hz, 1H), δ 5.95 (t, J=4.7 Hz, 1H), δ 5.72 (s, 1H), δ 3.92 (s, 3H), δ 3.88 (s, 3H), δ 3.86 (s, 3H), δ 2.88 (t, J=7.7 Hz, 2H), δ 2.4 (m, 2H).

d) Synthesis of Dihydronaphthalene Phosphate Prodrugs

Figure 6B:
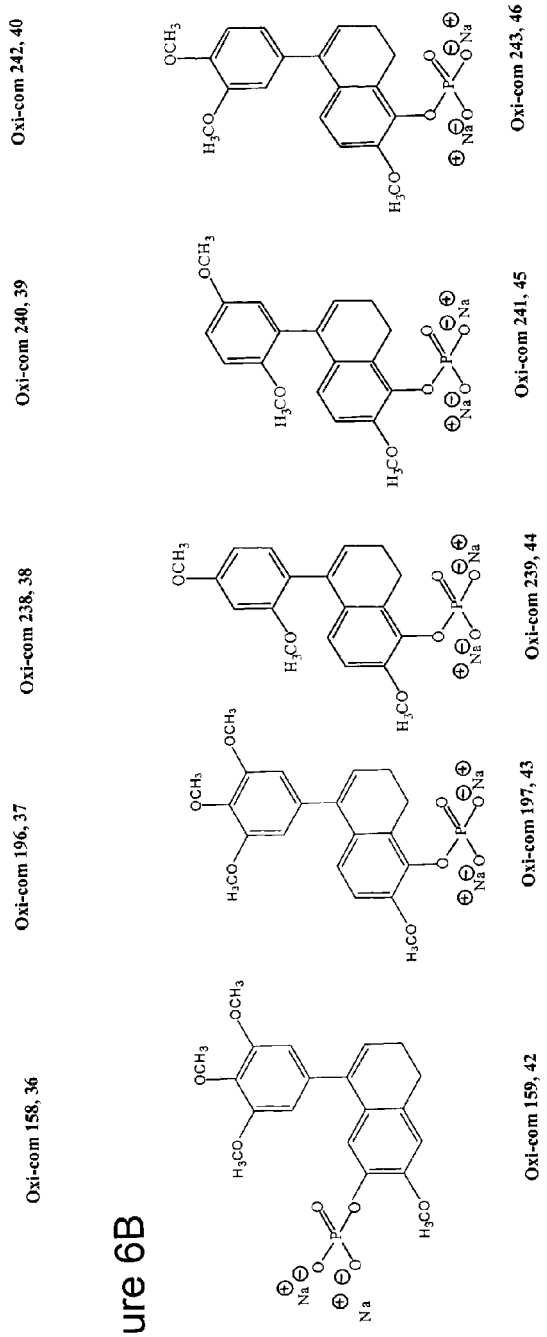

Phosphate Prodrugs in the form of phosphate salts and esters of hydroxyl functionalized dihydronaphthalene derivatives (and related phenolic analogs) are envisioned, for example phosphate ester disodium salts of C-5 (Oxi-com 197, 43) and C-7 Dihydronaphthalene (42) as illustrated in FIG. 6B. We have developed a synthetic route which will readily yield the C-5 disodium phosphate salt of dihydronapthalene by phosphorylation of 37 illustrated in FIG. 11.

The phenol Oxi-com 196 (37) was converted to its disodium phosphate prodrug salt using by sequential treatment of CCl4, iPr2Net, DMAP, and dibenzylphosphite in acetonitrole to produce the dibenzyl phosphate derivative (46) in 86% yield. The dibenzyl phosphate derivative was then stirred with NaI and TMSI in acetonitrile at RT for 30 min to debenzylate the compound. After removal of acetonitrile and drying, the residue was stirred overnight with NaOMe in methanol to form a salt. Crystallization in acetone-water produced the prodrug Oxi-com 197 (#?) as a white powder.

Oxi-com 197 (43): $^1$H-NMR (300 MHz) δ 2.31–2.35 (2H, m), 2.94 (2H, t, J=7.7 Hz), 3.80 (6H, s), 3.82 (6H, s), 6.07 (1H, t, J=4.3 Hz), 6.72–6.74 (4H, overlapping singlet and two doublets). $^{13}$C-NMR(90.55 MHz) δ 24.64, 25.32, 58.35, 58.81, 63.83, 109.08, 111.84, 123.63, 129.55, 131.00, 134.39, 138.61, 140.63, 141.40, 142.85, 154.49, 155.06. $^{31}$P-NMR(121.48 MHz) δ 4.33

Related phosphate prodrug derivatives of the 1-trimethoxyphenyl-dihydronapthalene system (FIG. 3B) were synthesized in a similar fashion.

Oxi-com 239 (44) $^1$H NMR (D$_2$O, 360 MHz): δ 7.22 (d, J=8.1 Hz, 1H), δ 6.72 (m, 3H), δ 6.46 (d, J=8.7 Hz, 1H), δ 5.99 (t, J=4.6 Hz, 1H), δ 3.91 (s, 3H), δ 3.82 (s, 3H), δ 3.71 (s, 3H), δ 3.05 (m, 2H), δ 2.39 (m, 2H). $^{31}$P NMR (D$_2$O, 360 MHz): δ 1.9 (s, 1P)

Oxi-com 241 (45) $^1$H NMR (D$_2$O, 360 MHz): δ 7.1 (d, J=9.0 Hz, 1H), δ 7.04 (dd, J=8.9 Hz, J=3.1 Hz, 3H), δ 6.93 (d, J=3.1 Hz, 1H), δ 6.74 (d, J=8.7, 1H), δ 6.45 (d, J=8.4 Hz, 1H), δ 6.0 (t, J=4.5 Hz, 1H), δ 3.83 (s, 3H), δ 3.81 (s, 3H), δ 3.67 (s, 3H), δ 3.07 (m, 2H), δ 2.4 (m, 2H). $^{31}$P NMR (D$_2$O, 360 MHz): δ 1.98 (s, 1P)

Figure 12:
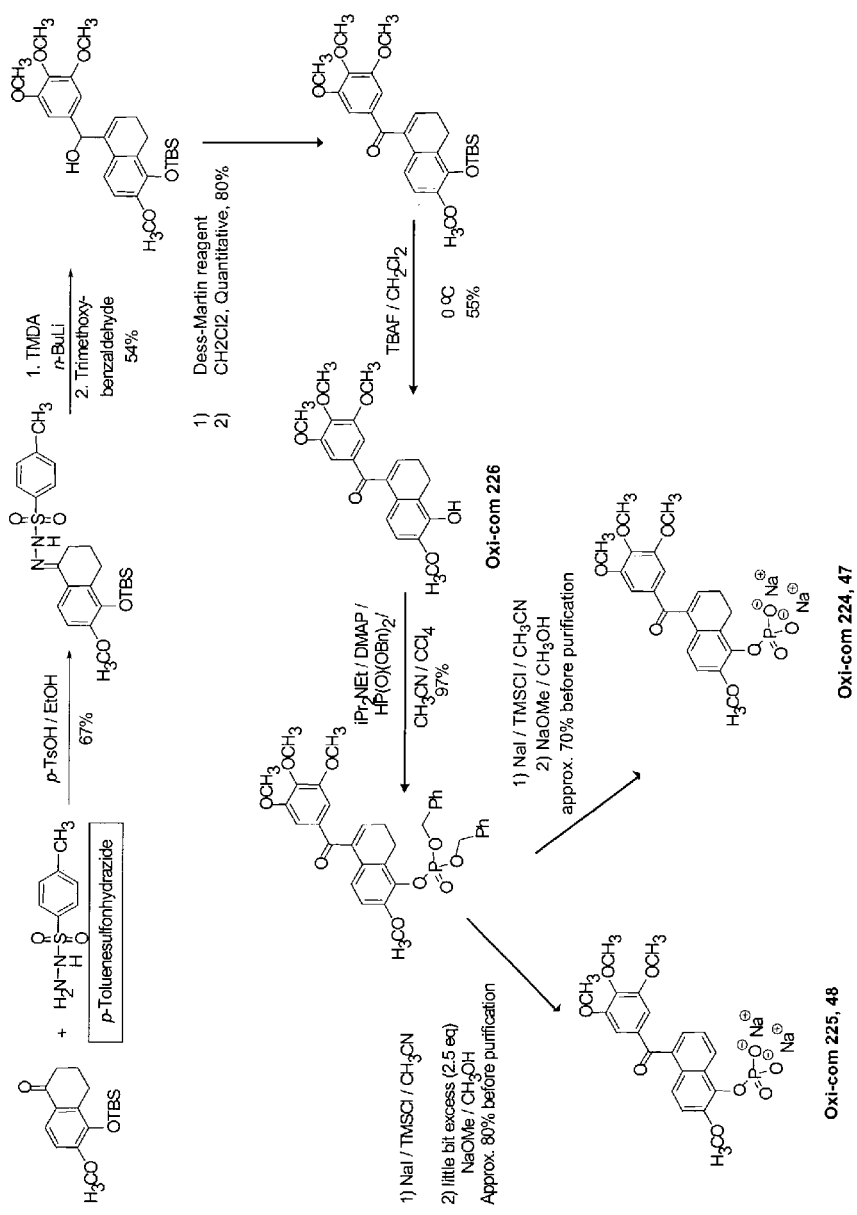
FIG. 12 illustrates a synthetic route for the preparation of an exemplary aroyl-substituted dihydronaphthalene, its corresponding phosphate prodrug, and an exemplary aroyl-substituted naphthalene phosphate prodrug.

Oxi-com 243 (46) $^1$H NMR (D$_2$O, 300 MHz): δ 7.1 (d, J=8.0 Hz, 1H), δ 7.02 (m, 2H), δ 6.79 (d, J=9.6 Hz, 1H), δ 6.76 (d, J=9.2 Hz, 1H), δ 6.08 (t, J=3.8 Hz, 1H), δ 3.9 (s, 3H), δ 3.84 (s, 3H), δ 3.81 (s, 3H), δ 3.07 (t, J=7.6 Hz, 2H), δ 2.32 (m, 2H). $^{31}$P NMR (D$_2$O, 300 MHz): δ 4.32 (s, 1P)

e) Synthesis of Hydroxy, Aroyl-Substituted Dihydronapthalene and Naphthalene Prodrugs Aryol-substituted dihydronaphthalene ligands have previously described in U.S. Pat. No. 6,162,930. Hydroxyl functionalized derivatives and corresponding phosphate prodrugs of this compound are now provided (see FIG. 7A). A detailed synthetic route for this compound is illustrated in FIG. 12.

Oxi-com 224 (47): $^1$H NMR: in D$_2$O δ (PPM) 7.07 (s, 2H, Ph-H̲), 6.80 (d, 1H, J=8.4 Hz, Ar—H̲), 6.72 (d, 1H, J=8.5 Hz, Ar—H̲), 6.45 (t, 1H, J=4.4 Hz, vinylic-H̲), 3.75 (s, 3H, —OCH̲$_3$), 3.74 (s, 9H, —OCH̲$_3$), 2.82 (t, 2H, J=7.7 Hz, —CH̲$_2$), 2.37(m, 2H, —CH̲$_2$) $^{31}$P NMR: in D$_2$O δ (PPM) −3.60 (not calibrated)

Phosphate prodrugs of hydroxyl functionalized naphthalene derivatives (and related phenolic analogs) are also provided in the present invention. An exemplary compound is depicted in FIG. 7B. This compound was synthesized as illustrated in FIG. 12.

Oxi-com 225 (48): $^1$H NMR in D$_2$O δ (PPM) 8.43 (d, 1H, J=8.6 Hz, Ar—H̲), 7.72 (d, 1H, J=9.2 Hz, Ar—H̲), 7.61 (t, 1H, J=6.9 Hz, Ar—H̲), 7.50 (d, 1H, J=6.7 Hz, Ar—H̲), 7.43 (d, 1H, J=9.3 Hz, Ar—H̲), 3.97 (s, 3H, —OCH̲$_3$), 3.87 (s, 3H, —OCH̲$_3$), 3.76 (s, 6H, —OCH̲$_3$) $^{31}$P NMR: in D$_2$O δ (PPM) −1.39 (not calibrated)

f) Synthesis of Diphosphate Prodrugs

Figure 13:
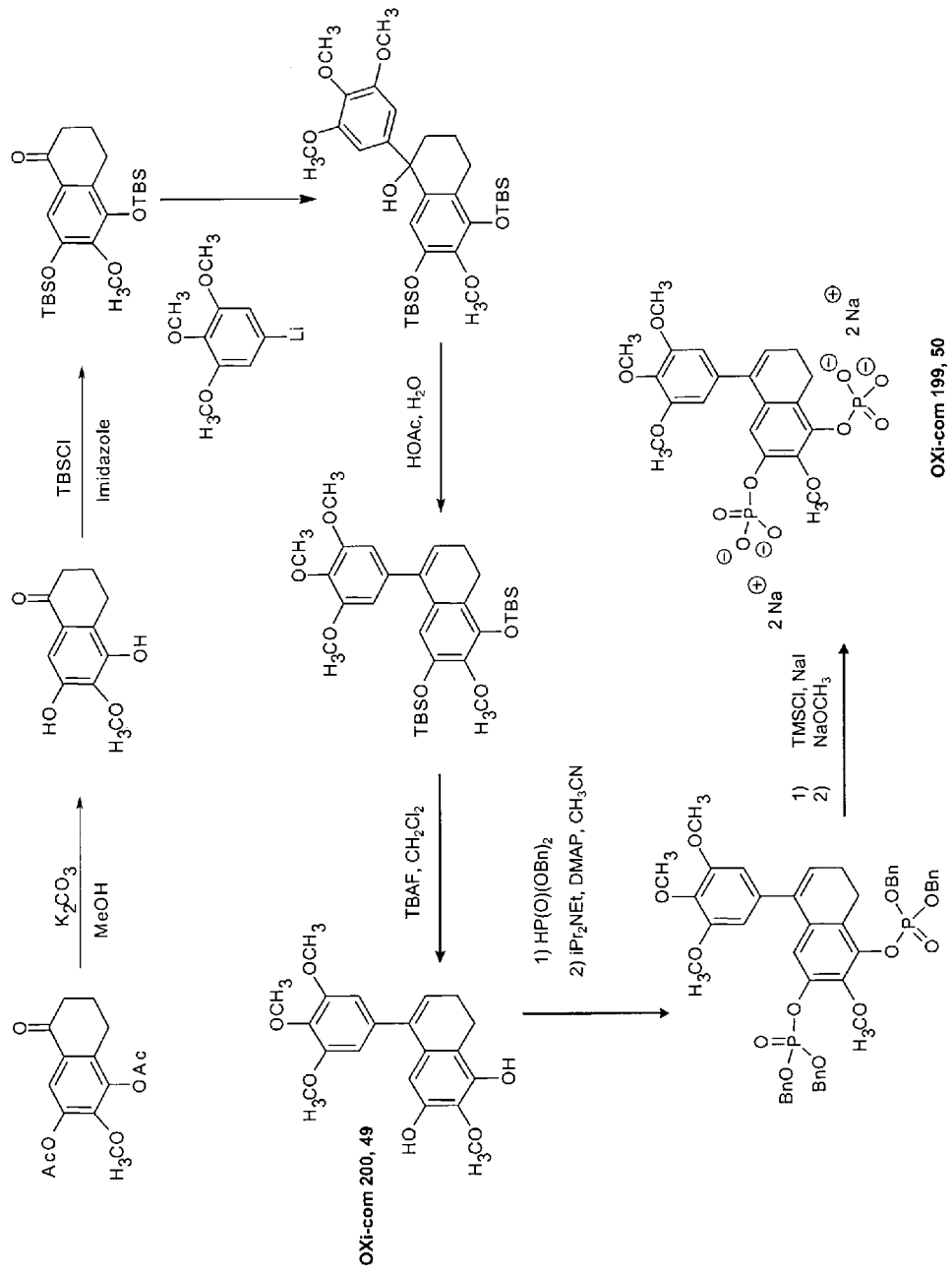
FIG. 13 illustrates a synthetic route for the preparation of an exemplary dihydroxy, aryl-substituted dihydronaphthalene tubulin binding agent and its corresponding diphosphate prodrug.

It is now known that while CA4P is a potent vascular targeting and destruction agent in vivo, it is likely that CA1P (a diphosphate) may prove to be as active or even more active than CA4P in vivo. Since CA4P is enzymatically converted to CA4, which in turn interacts with tubulin to cause vascular disruption, it is reasonable to expect that the new tubulin binding ligands described herein may prove to be enhanced vascular targeting agents once functionalized as diphosphates. The syntheses of these compounds will parallel the methodology described in the various synthetic schemes delineated within this application and will be readily apparent to persons skilled in the art. A representative synthesis is illustrated in FIG. 13.

Example 4

Inhibition of Tubulin Polymerization Assay

IC$_{50}$ values for tubulin polymerization were determined according to a previously described procedure (Bai et al, Cancer Research, 1996). Purified tubulin is obtained from bovine brain cells as described in Hamel and Lin (Hamel and Lin, Biochemistry, 1984). Various amounts of inhibitor were preincubated for 15 minutes at 37° C. with purified tubulin. After the incubation period, the reaction was cooled and GTP was added to induce tubulin polymerization. Polymerization was then monitored in a Gilford spectrophotometer at 350 nm. The final reaction mixtures (0.25 ml) contained 1.5 mg/ml tubulin, 0.6 mg/ml microtubule-associated proteins (MAPs), 0.5 mM GTP, 0.5 mM MgCl$_2$, 4% DMSO and 0.1M 4-morpholineethanesulfonate buffer (MES, pH 6.4). IC$_{50}$ is the amount of inhibitor needed to inhibit tubulin polymerization 50% with respect to the amount of inhibition that occurs in the absence of inhibitor.

TABLE 1

In Vitro Inhibition of Tubulin Polymerization.

| Compound | IC$_{50}$ (μM) |
| --- | --- |
| CA-4 | 1.2 (±0.02) |
| Oxi-com 141, 29 | 1–2 |
| Oxi-com 142, 31 | 0.5–1.0 |
| Oxi-com 143, 32 | Inactive (>40) |
| Oxi-com 196, 37 | 0.5–1 |
| Oxi-com 199, 50 | Inactive (>40) |

Example 5

In vitro Cytotoxicity Activity Against Cancer Cell Lines a) Human Cancer Cell Lines The activity of several compounds were tested against a variety of cell lines derived from human tumors, using an assay system similar to a procedure previously described (Monks et al, J. Natl. Cancer Inst., 1991). Briefly, the cell suspensions, diluted according to the particular cell type and the expected target cell density (5,000–40,000 cells per well based on cell growth characteristics), were added by pipet (100 μl) to 96-well microtiter plates. Inoculates were allowed a preincubation time of 24–28 hours at 37° C. for stabilization. Incubation with the inhibitor compounds lasted for 48 hours in 5% CO$_2$ atmosphere and 100% humidity. Determination of cell growth was performed by in situ fixation of cells, followed by staining with a protein-binding dye sulforhodamine B (SRB), which binds to the basic amino acids of cellular macromolecules. The solubilized stain was measured spectrophotometrically.

Several compounds were evaluated for cytotoxic activity against human P388 leukemia cell lines. The effective dose or ED$_{50}$ value (defined as the effective dosage required to inhibit 50% of cell growth) was measured. These and additional compounds were evaluated in terms of growth inhibitory activity against several other human cancer cell lines including: central nervous system ("CNS", SF-295), pancreas (BXPC-3), non-small cell lung cancer ("lung-NSC", NCI-H460), breast (MCF-7), colon (KM20L2), and prostate (DU-145). The results are described in Table 2 below. The growth inhibition $GI_{50}$ (defined as the dosage required to inhibit tumor cell growth by 50%) is listed for each cell line.

TABLE 2

In vitro Cytotoxicity against Human Cancer Cell Lines

| Compound | ED50 (ug/ml) for P-388 Cell Line | $GI_{50}$ (μg/ml) for Cell Line | | | | | |
|---|---|---|---|---|---|---|---|
| | | SF-295 | BXPC-3 | NCI-H460 | MCF-7 | KM20L2 | DU-145 |
| Oxi-com 156, | | 0.13 | 0.043 | 0.67 | 0.16 | 0.11 | 0.38 |
| Oxi-com 141, 29 | | 0.0033 | 0.0054 | 0.0038 | 0.0010 | 0.0032 | 0.0037 |
| Oxi-com 142, 31 | 0.034 | 0.0029 | 0.0034 | 0.0026 | <0.001 | 0.0027 | 0.0038 |
| Oxi-com 143, 32 | 20.4 | 2.2 | 2.0 | 3.4 | 3.0 | 2.5 | 2.8 |
| Oxi-com 158, 36 | | 5.4 | 1.8 | 3.2 | 1.5 | 2.6 | 3.4 |
| Oxi-com 196, 37 | 0.00175 | 0.00012 | 0.10 | 0.0032 | <0.0001 | 0.27 | 0.00040 |
| Oxi-com 197, 43 | 0.00182 | 0.0033 | 0.28 | 0.011 | 0.0045 | 0.33 | 0.0055 | b) Murine Cancer Cell Lines

The following compounds were tested for in vitro antiproliferative activity against the murine hemangioendothelioma MHEC-5T cell line using a standard MTT assay (see Mosman, J. Immunol. Methods, 1983). In actively proliferating cells, an increase in MTT conversion is spectrophotometrically quantified by the reduction of MTT (3-[4,5-dimethylthiazol-2-yl]-2,5-diphenyl tetrazolium bromide) to the insoluble formazan dye by enzymes associated with metabolic activity. A compound with growth inhibitory activity will cause a reduction in dye formation relative to cells exposed to a vehicle control. The $IC_{50}$ value (defined as the amount of compound required to inhibit growth of 50% of cells with respect to a control treatment) for each compound was determined at one hour and five days at (see Table 3 below).

TABLE 3

In vitro Cytotoxicity against Murine cancer cell lines

| Compound | $IC_{50}$ (μM) at 1 hour | $IC_{50}$ (μM) at 5 days |
|---|---|---|
| Oxi-com 196, 37 | 0.11 | 0.004 |
| Oxi-com 197, 43 | 0.10 | 0.003 |
| Oxi-com 199, 50 | >44.8 | >44.8 |
| Oxi-com 200, 49 | >50 | 16.2 |
| Oxi-com 224, 47 | 0.4 | 0.003 |
| Oxi-com 225, 48 | 0.4 | 0.005 |
| Oxi-com 229, 33 | >44 | >1.4 |
| Oxi-com 238, 38 | 14.0 | 0.04 |
| Oxi-com 239, 44 | 2.4 | 0.06 |
| Oxi-com 240, 39 | 8.0 | 0.03 |
| Oxi-com 241, 45 | 2.5 | 0.08 |
| Oxi-com 243, 46 | 20. | 0.30 |

Example 6

Inhibition of Tumor Blood Flow

The antivascular effects of the C-5 dihydronaphthalene phosphate prodrug Oxi-com 197, 43 was assessed in tumor-bearing mice using a Fluorescent Bead Assay. A MHEC-5T hemangioendothelioma tumor model was established by subcutaneous injection of 0.5×106 cultured transformed cell murine myocardial vascular endothelial cell line ("MHEC5-T") cells into the right flank of Fox Chase CB-17 Severe Combined Immunodeficient ("SCID") mice. When transplanted tumors reached a size of 500 mm³ (a size without development of necrosis), the mice received a single intraperitoneal (i.p.) injection of saline control or compound at doses ranging from 3.2 to 25 mg/kg. At 24 hours post-treatment, mice were injected intravenously with 0.25 ml of diluted FluoSphere beads (1:6 in physiological saline) in the tail vein, sacrificed after 3 minutes, and tumor was excised for cryosectioning. Tumor cryosections at a thickness of 8 um were directly examined using quantitative fluorescent microscopy. Blood vessels were indicated by blue fluorescence from injected beads. For quantification, image analysis of 3 sections from three tumors treated in each group were examined and vascular shutdown was expressed as vessel area (mm²) per tumor tissue area (mm²) as a percentage of the control ("% VAPM") and as vessel number per tumor tissue area (mm²) as a percentage of the control ("% VNPM"). The results as shown in Table 11 indicate a clear dose-dependent effect of the agent on tumor blood flow as indicated by the reduction in blood vessel number and vessel area. Administration of a 25 mg/kg dose of Oxi-com 197 was particularly effective, causing a 90% reduction in tumor vessel number relative to the control.

TABLE 4

Vascular Targeting Activity of Oxi-com 197 prodrug

| Dose (mg/kg) | % VAPM | % VNPM |
|---|---|---|
| 0 | 100 ± 13.5 | 100 ± 10.8 |
| 3.2 | 101.6 ± 36.6 | 89.1 ± 25.6 |
| 6.3 | 65.4 ± 4.9 | 66.5 ± 0.5 |
| 12.5 | 32.2 ± 6.8 | 55.5 ± 0.8 |
| 25 | 13.0 ± 5.0 | 10.4 ± 6.3 |

Additional compounds of the present invention were tested for antivascular effects at two dosages (100 mg/kg and 10 mg/kg) using the same Fluorescent Bead Assay as in the previous experiment. The results are summarized in Table 5 below.

TABLE 5

Vascular Targeting Activity of Aroyl dihydronaphthalene
and Aroyl Napthalene phosphate prodrugs

| Compound | % VAPM at 100 mg/kg dose | % VAPM at 10 mg/kg dose |
|---|---|---|
| Oxi-com 224, 47 | 46 | 17 |
| Oxi-com 225, 48 | 60 | 35 |

Example 7

Evaluation of Tumor Growth Control in Vivo

Figure 14:
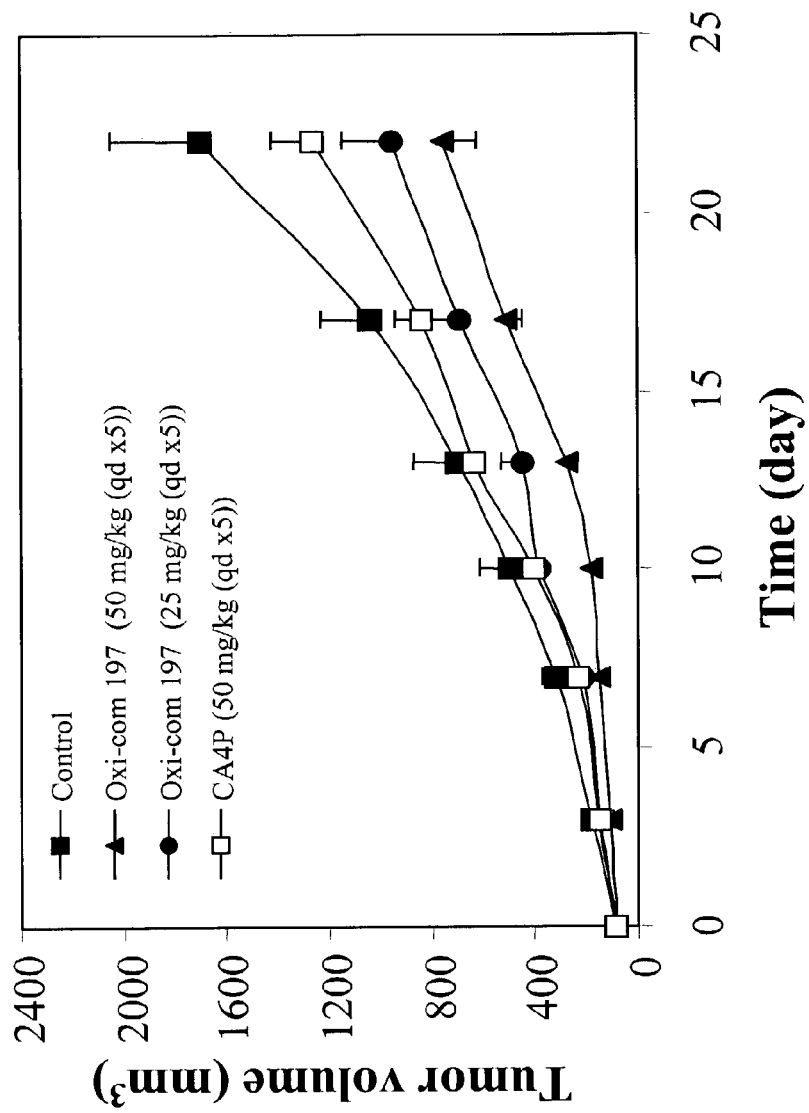
FIG. 14 is a graph depicting the in vivo tumor growth control activity of an exemplary hydroxy, aryl-substituted dihydronapthalene phosphate prodrug.

The antitumor activity of C-5 dihydronaphthalene phosphate prodrug, Oxi-com 197, was assessed in tumor-bearing mice by measuring its effects on tumor volume in comparison with CA4P. A human breast adenocarcinoma model was established by subcutaneous injection of cultured MDA-MB-231 cells in Fox Chase CB-17 SCID mice. When the average tumor size reached 50–100 mm$^3$, mice were randomly divided into several groups (n=10) with no significant difference in body weight and tumor size. Mice were administered CA4P or Oxi-com 197 in saline carrier at doses of 25, 50 or 100 mg/kg by daily intraperitoneal (i.p.) injection for 5 consecutive days (Q1×5). Saline carrier only was used as the control treatment. On Day 3, 7, 10, 13, 17 and 23, tumors were excised from animals in each treatment group (n=2) and measured by width and length. Tumor volume was calculated according to the following formula: Length×Width$^2$×0.4. The dosage effects of Oxi-com 197 is illustrated in FIG. 14. Administration of 25, 50, and 100 mg/kg doses of the drug significantly inhibited tumor growth relative to control treatment. C-5-DHN-P was also observed to have enhanced antitumor activity relative to CA4P.

OTHER EMBODIMENTS

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. For instance, in addition to the various metal salts described for the phosphates and phosphoramidates, any appropriate metal or non-metal cation and, in fact, any appropriately related salt construct can be employed without departing from the spirit and scope of the invention. For therapeutic and/or prophylactic anti-tumor purposes, the prodrugs of the present invention would be administered at a dosage of from about 5 mg/m$^2$ to about 100 mg/m$^2$ while intravascular infusion of the prodrug is preferred other modes of parenteral topical or enteral administration are usable under certain conditions.

The present invention also involves uses of the novel compounds described in manners relating to their useful effects on tubulin polymerization and abnormal vasculature. Certainly a method for inhibiting tubulin polymerization is a part of the present invention. This involves contacting a tubulin containing system with an effective amount of a compound described in the present invention. This tubulin containing system may be in a tumor cell, thereby inhibiting neoplastic disease by administering an effective amount of a compound of the present invention. Patients may thus be treated. In cases of cancer treatment, it is believed that many neoplasias such as leukemia, lung cancer, colon cancer, thyroid cancer, CNS, melanoma, ovarian cancer, renal cancer, prostate cancer and breast cancers may be effectively treated by the administration of an effective amounts of the compounds described in the present invention. Pharmaceutical preparations may be prepared by mixing the compounds of the present invention with a pharmaceutically acceptable carrier. This may be in tablet or intravascular form. In one important aspect, macular degeneration, and related diseases of the eye where vascularization is involved, may be treated by a method comprising administering an effective amount of a compound described in the present invention. Psoriasis may also be treated by administering an effective amount of the compound of the present invention. Likewise, any disease or condition caused or enhanced by undesired vascularization may be treated by administering an effective amount of a compound of the present invention.

In addition to their tumor-selective vascular targeting and destruction capabilities, it is contemplated that all the compounds of the present invention have potential application in the treatment of other diseases where the issue of vascularization is of great significance. Representative examples of these diseases include: diseases associated with ocular neovascularization (corneal and retinal), psoriasis and arthritis. All such similar substitutes and modifications apparent to those skilled in the art are deemed to be within the spirit, scope and concept of the invention as defined by the appended claims.

REFERENCES

The following citations are incorporated in pertinent part by reference herein for the reasons cited.

1. Bai, R.; Schwartz, R. E.; Kepler, J. A.; Pettit, G. R.; Hamel, E., Characterization of the Interaction of Cryptophycin with Tubulin: Binding in the Vinca Domain, Competitive Inhibition of Dolastatin 10 Binding, and an Unusual Aggregation Reaction, Cancer Res., 1996, 56, 4398–4406.
2. Boger, D. L.; Curran, T. T., Synthesis of the Lower Subunit of Rhizoxin, J. Org. Chem. 1992, 57, 2235.
3. Chaplin D J, Pettit G R, Hill S A. Anti-vascular approaches to solid tumor therapy: Evaluation of combretastatin A4 phophate. Anticancer Res., 1999; 19:189–196.
4. Chavan, A. J.; Richardson, S. K.; Kim, H.; Haley, B. E.; Watt, D. S., Forskolin Photoaffinity Probes for the Evaluation of Tubulin Binding Sites, Bioconjugate Chem. 1993, 4, 268.
5. Cortese, F.; Bhattacharyya, B.; Wolff, J., Podophyllotoxin as a Probe for the Colchicine Binding Site of Tubulin, J. Biol. Chem., 1977, 252, 1134.

6. Cushman, M.; Nagarathnam, D.; Gopal, D.; Chakraborti, A. K.; Lin, C. M.; Hamel, E. Synthesis and Evaluation of Stilbene and Dihydrostilbene Derivatives as Potential Anticancer Agents That Inhibit Tubulin Polymerization, *J. Med. Chem.* 1991, 34, 2579.
7. Dark, G. G., Hill, S. A., Prise, V. G., Tozer, G. M., Pettit, G. R., Chaplin, D. J., Combretastatin A-4, an Agent That Displays Potent and Selective Toxicity Toward Tumor Vasculature, *Cancer Res.*, 1997, 57, 1829–1834.
8. Davis P D, Dougherty G J, Blakey D C, Galbraith S M, Tozer G M, Holder A L, Naylor M A, Nolan J, Stratford M R, Chaplin D J, Hill S A. ZD6126: A Novel Vascular-targeting Agent that causes selective destruction of tumor vasculature. *Cancer Research.* 2002. 62(24): 7247–53.
9. Dorr, R. T.; Dvorakova, K.; Snead, K.; Alberts, D. S.; Salmon, S. E.; Pettit, G. R., Antitumor Activity of Combretastatin A4 Phosphate, a Natural Product Tubulin Inhibitor, *Invest. New Drugs*, 1996, 14, 131.
10. Floyd. L. J.; Barnes, L. D.; Williams, R. F., Photoaffinity Labeling of Tubulin with (2-Nitro-4-azidophenyl)deacetylcolchicine: Direct Evidence for Two Colchicine Binding Sites, *Biochemistry*, 1989, 28, 8515.
11. Gerwick, W. H.; Proteau, P. J.; Nagle, D. G.; Hamel, E.; Blokhin, A.; Slate, D. L., Structure of Curacin A, a Novel Antimitotic, Antiproliferative, and Brine Shrimp Toxic Natural Product from the Marine Cyanobacterium *Lyngbya majuscula*, *J. Org. Chem.* 1994, 59, 1243.
12. Hahn, K. M.; Hastie, S. B.; Sundberg, R. J., Synthesis and Evaluation of 2-Diazo-3,3,3-trifluoropropanoyl Derivatives of Colchicine and Podophyllotoxin as Photoaffinity Labels: Reactivity, Photochemistry, and Tubulin Binding, *Photochem. Photobiol.* 1992, 55, 17.
13. Hamel, E., Antimitotic Natural Products and Their Interactions with Tubulin, *Medicinal Research Reviews*, 1996, 16, 207.
14. Hamel, E.; Lin, C. M., Separation of Active Tubulin and Microtubule-Associated Proteins by Ultracentrifugation and Isolation of a Component Causing the Formation of Microtubule Bundles, *Biochemistry*, 1984, 23, 4173–4184.
15. Hammonds, T. R.; Denyer, S. P.; Jackson, D. E.; Irving, W. L., Studies To Show That With Podophyllotoxin the Early Replicative Stages of Herpes Simplex Virus Type 1 Depend Upon Functional Cytoplasmic Microtubules, *J. Med. Microbiol.*, 1996, 45, 167.
16. Iyer S, Chaplin D J, Rosenthal D S, et al. Induction of apoptosis in proliferating human endothelial cells by the tumor-specific antiangiogenesis agent combretastatin A-4. *Cancer Res.* 1998; 58:4510–4514.
17. Jiang, J. B.; Hesson, D. P.; Dusak, B. A.; Dexter, D. L.; Kang, G. J.; Hamel, E., Synthesis and Biological Evaluation of 2-Styrylquinazolin-4(3H)-ones, a New Class of Antimitotic Anticancer Agents Which Inhibit Tubulin Polymerization, *J. Med. Chem.* 1990, 33, 1721.
18. Kanthou C, Tozer G M. The tumor vascular targeting agent CA4P induces reorganization of the actin cytoskeleton and early membrane blebbing in human endothelial cells. *Blood.* 2002. 99(6):2060–9.
19. Kingston, D. G. I.; Samaranayake, G.; Ivey, C. A., The Chemistry of Taxol, a Clinically Useful Anticancer Agent, *J. Nat. Prod.* 1990, 53, 1.
20. Kobayashi, S.; Nakada, M.; Ohno, M., Synthetic Study on an Antitumor Antibiotic Rhizoxin by Using an Enzymatic Process on Prochiral beta-Substituted Glutarates, *Pure Appl. chem.* 1992, 64, 1121.
21. Kobayashi, S.; Nakada, M.; Ohno, M., Synthetic Study on an Antitumor Antibiotic Rhizoxin by Using an Enzymatic Process on Prochiral beta-Substituted Glutarates *Indian J. Chem., Sect. B.* 1993, 32B, 159.
22. Lavielle, G.; Havtefaye, P.; Schaeffer, C.; Boutin, J. A.; Cudennec, C. A.; Pierre, A., New α-Amino Phosphonic Acid Derivatives of Vinblastine: Chemistry and Antitumor Activity, *J. Med. Chem.* 1991, 34, 1998.
23. Lejeune P, Hodge T G, Vrignaud, Bissery M-C. In vivo antitumor activity and tumor necrosis induced by AVE8062A, a tumor vasculature targeting agent. Proceedings of the AACR. ABSTRACT#781. 2002, 43: 156.
24. Lin, C. M.; Ho, H. H.; Pettit, G. R.; Hamel, E., Antimitotic Natural Products Combretastatin A-4 and Combretastatin A-2: Studies on the Mechanism of Their Inhibition of the Binding of Colchicine to Tubulin, *Biochemistry* 1989, 28, 6984.
25. Monks, A.; Scudiero, D.; Skehan, P.; Shoemaker, R.; Paull, K.; Vistica, D.; Hose, C.; Langley, J.; Cronise, P.; Vaigro-Wolff, A.; Gray-Goodrich; Campbell; Mayo; Boyd, M., Feasibility of a High-Flux Anticancer Drug Screen Using a Diverse Panel of Cultured Human Tumor Cell Lines, *J. Natl. Cancer Inst.*, 1991, 83, 757–766.
26. Mossman, T. Rapid colorimetric assay for cellular growth and survival: application to proliferation and cytotoxicity assay. *J. Immunol. Methods*, 1983, 16, 195–200.
27. Nakada, M.; Kobayashi, S.; Iwasaki, S.; Ohno, M., The First Total Synthesis of the Antitumor Macrolide Rhizoxin: Synthesis of the Key Building Blocks, *Tetrahedron Lett.* 1993, 34, 1035.
28. Nicolaou, K. C., Winssinger, N., Pastor, J., Ninkovic, S., Sarabia, F., He, Y., Vourloumis, D., Yang, Z., Oi, T., Giannakakou, P., Hamel, E., Synthesis of Epothilones A and B in Solid and Solution Phase, *Nature*, 1997, 387, 268–272.
29. Nogales, E., Wolf, S. G., and Downing, K. H., Structure of the α,β Tubulin Dimer by Electron Crystallography, *Nature*, 1998, 391, 199–203.
30. Owellen, R. J.; Hartke, C. A.; Kickerson, R. M.; Hains, F. O., Inhibition of Tubulin-Microtubule Polymerization by Drugs of the Vinca Alkaloid Class, *Cancer Res.* 1976, 36, 1499.
31. Pettit, G. R.; Rhodes, M. R., Antineoplastic agents 393. Synthesis of the trans-isomer of CA4P. *Anti-Cancer Drug Des.*, 1998, 13, 183.
32. Pettit, G. R., Srirangam, J. K., Barkoczy, J., Williams, M. D., Boyd, M. R., Hamel, E., Pettit, R. K., Hogan F., Bai, R., Chapuis, J. C., McAllister, S. C., Schmidt, J. M., Antineoplastic Agents 365: Dolastatin 10 SAR Probes, *Anti-Cancer Drug Des.*, 1998, 13, 243–277.
33. Pettit, G. R., Toki, B., Herald, D. L., Verdier-Pinard, P., Boyd, M. R., Hamel, E., Pettit, R. K., Antineoplastic Agents 379. Synthesis of Phenstatin Phosphate, *J. Med. Chem.*, 1998, 41, 1688–1695.
34. Pettit, G. R.; Cragg, G. M.; Singh, S. B., Antineoplastic agents, 122. Constituents of Combretum caffrum, *J. Nat. Prod.* 1987, 50, 386.
35. Pettit, G. R., Kamano, Y., Herald, C. L., Tuinman, A. A., Boettner, F. E., Kizu, H., Schmidt, J. M., Baczynskyj, L., Tomer, K. B., Bontems, R. J., The Isolation and Structure of a Remarkable Marine Animal Antineoplastic Constituent: Dolastatin 10, *J. Am. Chem. Soc.*, 1987, 109, 6883–6885.

36. Pettit, G. R.; Singh, S. B.; Cragg, G. M., Synthesis of Natural (−)-Combretastatin, *J. Org. Chem.* 1985, 50, 3404.
37. Pettit, G. R.; Cragg, G. M.; Herald, D. L.; Schmidt, J. M.; Lohavanijaya, P., Isolation and Structure of combretastatin, *Can, J. Chem.* 1982, 60, 1374.
38. Rao, A. V. R.; Bhanu, M. N.; Sharma, G. V. M., Studies Directed Towards the Total Synthesis of Rhizoxin: Stereoselective Synthesis of C-12 to C-18 Segment, *Tetrahedron Lett.* 1993, 34, 707.
39. Rao, S.; Horwitz, S. B.; Ringel, I., Direct Photoaffinity Labeling of Tubulin with Taxol, *J. Natl. Cancer Inst.*, 1992, 84, 785.
40. Rao, A. V. R.; Sharma, G. V. M.; Bhanu, M. N., Radical Mediated Enantioselective Construction of C-1 to C-9 Segment of Rhizoxin, *Tetrahedron Lett.* 1992, 33, 3907.
41. Safa, A. R.; Hamel, E.; Felsted, R. L., Photoaffinity Labeling of Tubulin Subunits with a Photoactive Analog of Vinblastine, *Biochemistry* 1987, 26, 97.
42. Sawada, T.; Kato, Y.; Kobayashi, H.; Hashimoto, Y.; Watanabe, T.; Sugiyama, Y.; Iwasaki, S., A Fluorescent Probe and a Photoaffinity Labeling Reagent to Study the Binding Site of Maytansine and Rhizoxin on Tubulin, *Bioconjugate Chem.*, 1993, 4, 284. 31.
43. Sawada, T.; Kobayashi, H.; Hashimoto, Y.; Iwasaki, S., Identification of the Fragment Photoaffinity-labeled with Azidodansyl-rhizoxin as Met-363-Lys-379 on beta-Tubulin, *Biochem. Pharmacol.* 1993, 45, 1387.
44. Schiff, P. B.; Fant, J.; Horwitz, S. B., Promotion of Microtubule Assembly In Vitro by Taxol, *Nature*, 1979, 277, 665.
45. Staretz, M. E.; Hastie, S. B., Synthesis, Photochemical Reactions, and Tubulin Binding of Novel Photoaffinity Labeling Derivatives of Colchicine, *J. Org. Chem.* 1993, 58, 1589.
46. Swindell, C. S.; Krauss, N. E.; Horwitz, S. B.; Ringel, I., Biologically Active Taxol Analogs with Deleted A-ring Side Chain Substituents and Variable C-2' Configurations, *J. Med. Chem.* 1991, 34, 1176. (d) Parness, J.; Horwitz, S. B., Taxol Binds to Polymerized Tubulin In Vitro, *J. Cell Biol.* 1981, 91, 479.
47. Tozer, G. M.; Prise, V. E.; Wilson, J.; Locke, R. J.; Vojnovic, B.; Stratford, M. R. L.; Dennis, M. F.; Chaplin, D. J., Combretastatin A-4 Phosphate as a Tumor Vascular-Targeting Agent: Early Effects in Tumors and Normal Tissues. *Cancer Res.*, 1999, 59, 1626.
48. Williams, R. F.; Mumford, C. L.; Williams, G. A.; Floyd, L. J.; Aivaliotis, M. J.; Martinez, R. A.; Robinson, A. K.; Barnes, L. D., A Photoaffinity Derivative of Colchicine: 6-(4'-Azido-2'-nitrophenylamino)hexanoyldeacetyl-colchicine: Photolabeling and Location of the Colchicine-binding Site on the alpha-subunit of Tubulin, *J. Biol. Chem.* 1985, 260, 13794.
49. Zhang, X.; Smith, C. D., Microtubule Effects of Welwistatin, a Cyanobacterial Indolinone that Circumvents Multiple Drug Resistance, *Molecular Pharmacology*, 1996, 49, 288.

What is claimed is:

1. A compound of the formula:

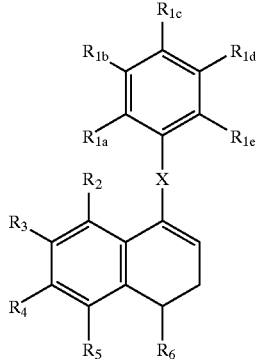

(Ia)

wherein:
$R_{1a}$, $R_{1b}$, $R_{1c}$, and $R_{1e}$, are independently selected from the group consisting of H, halogen, lower alkyl, or lower alkoxy;
$R_{1d}$ is H;
$R_2$ through $R_6$ are independently selected from the group consisting of H, OH, halogen, amine, lower alkyl, lower alkoxy, phosphate, phosphoramidate, or amino acid acyl; and
X is a single covalent bond or a carbonyl group.

2. The compound of claim 1, wherein:
$R_{1a}$, $R_{1b}$, and $R_{1c}$ are all methoxy and the remaining $R_{1e}$ and $R_{1d}$ are H,
One of $R_2$ through $R_5$ is a methoxy and the remaining $R_2$ through $R_6$ are H; and
X is a single covalent bond.

3. The compound of claim 2, wherein:
$R_3$ is methoxy and the remaining $R_2$ through $R_6$ are H.

4. The compound of claim 2, wherein:
$R_4$ is methoxy and the remaining $R_2$ through $R_6$ are H.

5. The compound of claim 2, wherein:
$R_5$ is methoxy and the remaining $R_2$ through $R_6$ are H.

6. A compound of the formula:

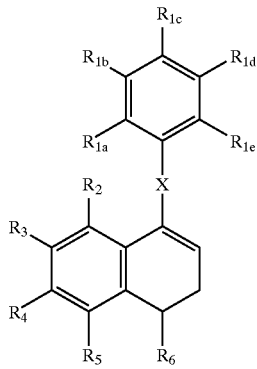

(Ia)

wherein:
Two of $R_{1a-e}$ are methoxy and the remaining $R_{1a-e}$ are H,
One of $R_2$ through $R_6$ is a methoxy,
and at least one of the remaining $R_2$ through $R_6$ is selected from the group consisting of OH, halogen, amine, lower alkoxy, phosphate, phosphoramidate, or amino acid acyl, and the remaining $R_2$ through $R_6$ are H; and X is a single covalent bond.

7. The compound of claim 6, wherein:
$R_{1a}$, $R_{1c}$, and $R_4$ are methoxy, $R_5$ is an OH or a phosphate; and $R_1b$, $R_{1e\text{-}d}$ and the remaining $R_2$ through $R_6$ are H.

8. The compound of claim 6, wherein:
$R_{1a}$, $R_{1d}$, and $R_4$ are methoxy, $R_5$ is an OH or a phosphate; and $R_{1b\text{-}c}$, $R_{1e}$ and the remaining $R_2$ through $R_6$ are H.

9. The compound of claim 6, wherein:
$R_{1b\text{-}c}$ and $R_4$ are methoxy, $R_5$ is an OH or a phosphate; and $R_{1a}$, $R_{1d\text{-}e}$ and the remaining $R_2$ through $R_6$ are H.

10. The compound of claim 6, wherein:
$R_4$ is methoxy, $R_5$ is an amine, phosphoramidate, or amino acid acyl; and the remaining $R_2$ through $R_6$ are H.

11. A compound of the formula Ia:

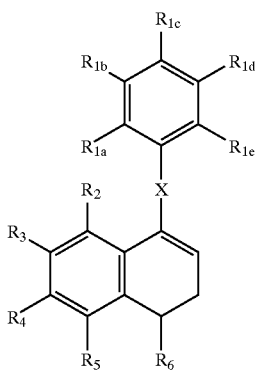

(Ia)

wherein:
Two of $R_{1a\text{-}e}$ are methoxy and the remaining $R_{1a\text{-}c}$ are H,
One of $R_2$ through $R_6$ is a methoxy,
and at least one of the remaining $R_2$ through $R_6$ is selected from the group consisting of OH, halogen, amine, lower alkoxy, phosphate, phosphoramidate, or amino acid acyl, and the remaining $R_2$ through $R_6$ are H;
and X is a carbonyl.

12. The compound of claim 11, wherein:
$R_4$ is methoxy, $R_5$ is OH or phosphate; and the remaining $R_2$ through $R_6$ are H.

13. A compound of the formula:

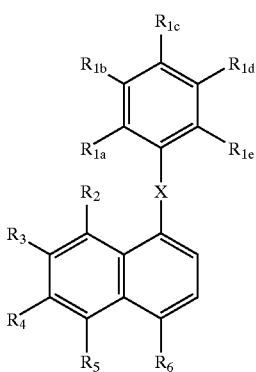

(Ib)

wherein:
$R_{1a}$, $R_{1b}$, $R_{1c}$, $R_{1d}$, and $R_{1e}$ are independently selected from the group consisting of H, halogen, lower alkyl, or lower alkoxy,
$R_2$ through $R_6$ are independently selected from the group consisting of H, OH, halogen, amine, lower alkyl, lower alkoxy, phosphate, phosphoramidate, or amino acid acyl; and
X is a carbonyl group.

14. The compound of claim 13, wherein:
At least two of $R_{1a\text{-}f}$ are methoxy and the remaining $R_{1a\text{-}f}$ are H,
One of $R_2$ through $R_6$ is a methoxy,
and at least one of the remaining $R_2$ through $R_6$ is selected from the group consisting of OH, halogen, amine, lower alkoxy, phosphate, phosphoramidate, or amino acid acyl, and the remaining $R_2$ through $R_6$ are H.

15. The compound of claim 14, wherein:
$R_{1b\text{-}d}$ and $R_4$ are methoxy, $R_5$ is OH or phosphate; and $R_{1a}$, $R_{1e}$ and the remaining $R_2$ through $R_6$ are H.

16. A method for treating a vascular proliferative disorder in an animal comprising administering to an animal an effective amount of a compound of claim 1.

17. The method of claim 16, wherein the vascular proliferative disorder is characterized by the presence of malignant proliferating vasculature.

18. The method of claim 17, wherein the malignant proliferating vasculature is associated with a tumor or other neoplastic disease.

19. The method of claim 16, wherein the vascular proliferative disorder is characterized by the presence of nonmalignant proliferating vasculature.

20. The method of claim 19, wherein the nonmalignant proliferating vasculature is associated with an ocular disease selected from the group comprising wet or age-related macular degeneration, diabetic retinopathy, retinopathy of prematurity, diabetic macular edema, uveitis, or corneal neovascularization.

21. The method of claim 19, wherein the nonmalignant proliferating vasculature is associated with a nonocular disease state such as psoriasis, rheumatoid arthritis, atheroma, restenosis, Kaposi's sarcoma, haemangioma, and in general, inflammatory diseases characterized by vascular proliferation.

22. A method for selectively reducing the flow of blood to at least a portion of a neoplastic region, comprising administering a compound of claim 1 and thereby causing substantial necrosis of tissue in the neoplastic region without substantial necrosis of tissue in adjoining regions.

23. The method of claim 22, wherein the reduction in tumor blood flow is reversible such that normal tumor blood flow is restored following cessation of treatment.

24. A method for treating neoplastic disease in an animal comprising administering to an animal an antiproliferative amount of a compound of claim 1.

25. The method of claim 24, wherein the compound has the direct result of causing tumor cell cytotoxicity due to inhibition of mitosis.

26. A method for inhibiting tubulin polymerization by contacting a tubulin-containing system with a compound of claim 1.

27. The method of claim 26, wherein said system is a tumor cell.

28. A pharmaceutical formulation containing a compound of claim 1 in a pharmaceutically suitable carrier.

* * * * *